(12) United States Patent
Sherwood et al.

(10) Patent No.: US 11,389,465 B2
(45) Date of Patent: Jul. 19, 2022

(54) PHOSPHORYLATED HEXAACYL DISACCHARIDES (PHADS) FOR TREATING OR PREVENTING INFECTIONS

(71) Applicant: VANDERBILT UNIVERSITY, Nashville, TN (US)

(72) Inventors: Edward Sherwood, Nashville, TN (US); Antonio Hernandez, Franklin, TN (US); Julia Bohannon, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/610,125

(22) PCT Filed: May 1, 2018

(86) PCT No.: PCT/US2018/030349
§ 371 (c)(1),
(2) Date: Nov. 1, 2019

(87) PCT Pub. No.: WO2018/204302
PCT Pub. Date: Nov. 8, 2018

(65) Prior Publication Data
US 2020/0085850 A1 Mar. 19, 2020

Related U.S. Application Data

(60) Provisional application No. 62/492,451, filed on May 1, 2017.

(51) Int. Cl.
A61K 31/7016 (2006.01)
A61P 31/04 (2006.01)
A61K 45/06 (2006.01)

(52) U.S. Cl.
CPC .......... *A61K 31/7016* (2013.01); *A61K 45/06* (2013.01); *A61P 31/04* (2018.01)

(58) Field of Classification Search
CPC ...... A61K 31/7016; A61K 45/06; A61P 31/04
USPC .......................................................... 514/53
See application file for complete search history.

(56) References Cited

U.S. PATENT DOCUMENTS

| | | |
|---|---|---|
| 4,235,871 A | 11/1980 | Papahadjopoulous et al. |
| 5,008,050 A | 4/1991 | Cullis et al. |
| 5,888,519 A | 3/1999 | Alving |
| 6,113,918 A | 9/2000 | Johnson et al. |
| 6,303,347 B1 | 10/2001 | Johnson et al. |
| 2002/0028209 A1 | 3/2002 | Garcon-Johnson et al. |
| 2016/0220666 A1 | 8/2016 | Sequoia et al. |

FOREIGN PATENT DOCUMENTS

| | | |
|---|---|---|
| WO | 98/50399 | 11/1998 |
| WO | 01/34617 | 5/2001 |
| WO | 01/90129 | 11/2001 |
| WO | 02/12258 | 2/2002 |
| WO | 2005/081872 | 9/2005 |
| WO | 2007/068411 | 6/2007 |

OTHER PUBLICATIONS

LaBauve et al. (Current Protocols in Microbiology 6E.1.1-6E.1.8, May 2012).*
International Search Report and Written Opinion dated Jul. 20, 2018, from International Application No. PCT/US2018/030349, 9 pages.
Alving, C. R. et al. "Liposomal Vaccine Adjuvant Formulations", Rev. Roum. Chim., 2016, 61(8-9), 631-635.
Portuondo, D. L. et al. "Adjuvants and delivery systems for antifungal vaccines: Current state and future developments", Medical Mycology, 2015, 53, 69-89.
Johnson, D. A. et al. "3-O-Desacyl Monophosphoryl Lipid A Derivatives: Synthesis and Immunostimulant Activities", J. Med. Chem. 1999, 42, 4640-4649.
Cen, H., Z. Wu, F. Wang, and C. Han. 2015. Pathogen distribution and drug resistance in a burn ward: a three-year retrospective analysis of a single center in China. Int J Clin Exp Med 8: 19188-19199.
Gladki, A., S. Kaczanowski, P. Szczesny, and P. Zielenkiewicz. 2013. The evolutionary rate of antibacterial drug targets. BMC Bioinformatics 14: 36.
Sun, H. Y., S. Fujitani, R. Quintiliani, and V. L. Yu. 2011. Pneumonia due to Pseudomonas aeruginosa: part II: antimicrobial resistance, pharmacodynamic concepts, and antibiotic therapy. Chest 139: 1172-1185.
Williams, F. N., D. N. Herndon, H. K. Hawkins, J. O. Lee, R. A. Cox, G. A. Kulp, C. C. Finnerty, D. L. Chinkes, and M. G. Jeschke. 2009. The leading causes of death after burn injury in a single pediatric burn center. Crit Care 13: R183.
George, A. J., A. K. Boehme, J. E. Siegler, D. Monlezun, B. D. Fowler, A. Shaban, K. C. Albright, T. M. Beasley, and S. Martin-Schild. 2013. Hospital-Acquired Infection Underlies Poor Functional Outcome in Patients with Prolonged Length of Stay. ISRN Stroke 2013.
Wenzel, R. P., and M. B. Edmond. 2001. The impact of hospital-acquired bloodstream infections. Emerg Infect Dis 7: 174-177.
Klevens, R. M., J. R. Edwards, and R. P. Gaynes. 2008. The impact of antimicrobial-resistant, health care-associated infections on mortality in the United States. Clin Infect Dis 47: 927-930.
Shlaes, D. M., D. Sahm, C. Opiela, and B. Spellberg. 2013. The FDA reboot of antibiotic development. Antimicrob Agents Chemother 57: 4605-4607.
Geyik, M. F., M. Aidemir, S. Hosoglu, and H. I. Tacyildiz. 2003. Epidemiology of burn unit infections in children. Am J Infect Control 31: 342-346.
Gang, R. K., R. L. Bang, S. C. Sanyal, E. Mokaddas, and A. R. Lari. 1999. Pseudomonas aeruginosa septicaemia in burns. Burns 25: 611-616.

(Continued)

Primary Examiner — Shaojia A Jiang
Assistant Examiner — Michael C Henry
(74) Attorney, Agent, or Firm — Meunier Carlin & Curfman LLC

(57) ABSTRACT

The present disclosure relates to phosphorylated hexaacyl disaccharide (PHAD) compounds, compositions, and methods for treating or preventing infections.

16 Claims, 27 Drawing Sheets

(56) References Cited

OTHER PUBLICATIONS

Bang, R. L., P. N. Sharma, S. C. Sanyal, S. Bang, and M. K. Ebrahim. 2004. Burn septicaemia in Kuwait: associated demographic and clinical factors. Med Prine Pract 13: 136-141.
Laird, M. H., S. H. Rhee, D. J. Perkins, A. E. Medvedev, W. Piao, M. J. Fenton, and S. N. Vogel. 2009. TLR4/MyD88/PI3K interactions regulate TLR4 signaling. J Leukoc Biol 85: 966-977.
Bohannon, J. K., A. Hernandez, P. Enkhbaatar, W. L. Adams, and E. R. Sherwood. 2013. The immunobiology of toll-like receptor 4 agonists: from endotoxin tolerance to immunoadjuvants. Shock 40: 451-462.
Murphey, E. D., G. Fang, T. K. Varma, and E. R. Sherwood. 2007. Improved bacterial clearance and decreased mortality can be induced by LPS tolerance and is not dependent upon IFN-gamma. Shock 27: 289-295.
Murphey, E. D., G. Fang, and E. R. Sherwood. 2008. Endotoxin pretreatment improves bacterial clearance and decreases mortality in mice challenged with *Staphylococcus aureus*. Shock 29: 512-518.
Varma, T. K., M. Durham, E. D. Murphey, W. Cui, Z. Huang, C. Y. Lin, T. Toliver-Kinsky, and E. R. Sherwood. 2005. Endotoxin priming improves clearance of Pseudomonas aeruginosa in wild-type and interleukin-10 knockout mice. Infect Immun 73: 7340-7347.
Lembo, A., M. Pelletier, R. Iyer, M. Timko, J. C. Dudda, T. E. West, C. B. Wilson, A. M. Hajjar, and S. J. Skerrett. 2008. Administration of a synthetic TLR4 agonist protects mice from pneumonic tularemia. J Immunol 180: 7574-7581.
Romero, C. D., T. K. Varma, J. B. Hobbs, A. Reyes, B. Driver, and E. R. Sherwood. 2011. The Toll-like receptor 4 agonist monophosphoryl lipid a augments innate host resistance to systemic bacterial infection. Infect Immun 79: 3576-3587.
Metkar, S., K. S. Kim, J. Silver, and S. M. Goyert. 2012. Differential expression of CD14-dependent and independent pathways for chemokine induction regulates neutrophil trafficking in infection. J Leukoc Biol 92: 389-396.
Hernandez, A., J. K. Bohannon, L. Luan, B. A. Fensterheim, Y. Guo, N. K. Patil, C. McAdams, J. Wang, and E. R. Sherwood. 2016. The role of MyD88- and TRIF-dependent signaling in monophosphoryl lipid A-induced expansion and recruitment of innate immunocytes. J Leukoc Biol.
Bohannon, J. K., L. Luan, A. Hernandez, A. Afzal, Y. Guo, N. K. Patil, B. Fensterheim, and E. R. Sherwood. 2015. Role of G-CSF in monophosphoryl lipid A-mediated augmentation of neutrophil functions after burn injury. J Leukoc Biol.
Krakauer, T., M. J. Buckley, and D. Fisher. 2010. Proinflammatory mediators of toxic shock and their correlation to lethality. Mediators Inflamm 2010: 517594.
Kiener, P. A., F. Marek, G. Rodgers, P. F. Lin, G. Warr, and J. Desiderio. 1988. Induction of tumor necrosis factor, IFN-gamma, and acute lethality in mice by toxic and non-toxic forms of lipid A. J Immunol 141: 870-874.
Astiz, M. E., E. C. Rackow, J. G. Still, S. T. Howell, A. Cato, K. B. Von Eschen, J. T. Ulrich, J. A. Rudbach, G. McMahon, R. Vargas, and et al. 1995. Pretreatment of normal humans with monophosphoryl lipid A induces tolerance to endotoxin: a prospective, double-blind, randomized, controlled trial. Crit Care Med 23: 9-17.
Bentala, H., W. R. Verweij, A. Huizinga-Van der Viag, A. M. van Loenen-Weemaes, D. K. Meijer, and K. Poelstra. 2002. Removal of phosphate from lipid A as a strategy to detoxify lipopolysaccharide. Shock 18: 561-566.
Henricson, B. E., W. R. Benjamin, and S. N. Vogel. 1990. Differential cytokine induction by doses of lipopolysaccharide and monophosphoryl lipid A that result in equivalent early endotoxin tolerance. Infect Immun 58: 2429-2437.
Monie, A., C. F. Hung, R. Roden, and T. C. Wu. 2008. Cervarix: a vaccine for the prevention of HPV 16, 18-associated cervical cancer. Biologies 2: 97-105.
Bosch, F. X., S. de Sanjose, and X. Castellsague. 2011. The prospects of HPV vaccination in cervical cancer prevention: results of a new independent trial. Cancer Discov 1: 377-380.
Bohannon, J., W. Cui, R. Cox, R. Przkora, E. Sherwood, and T. Toliver-Kinsky. 2008. Prophylactic treatment with fms-like tyrosine kinase-3 ligand after burn injury enhances global immune responses to infection. Journal of immunology 180: 3038-3048.
Bohannon, J., W. Cui, E. Sherwood, and T. Toliver-Kinsky. 2010. Dendritic cell modification of neutrophil responses to infection after burn injury. Journal of immunology 185: 2847-2853.
Redl, H., S. Bahrami, G. Schlag, and D. L. Traber. 1993. Clinical detection of LPS and animal models of endotoxemia. Immunobiology 187: 330-345.
Nakazawa, H., H. Noda, S. Noshima, J. T. Flynn, L. D. Traber, D. N. Herndon, and D. L. Traber. 1993. Pulmonary transvascular fluid flux and cardiovascular function in sheep with chronic sepsis. J Appl Physiol 75: 2521-2528.
Enkhbaatar, P., K. Murakami, L. D. Traber, R. Cox, J. F. Parkinson, M. Westphal, A. Esechie, N. Morita, M. O. Maybauer, D. M. Maybauer, A. S. Burke, F. C. Schmalstieg, H. K. Hawkins, D. N. Herndon, and D. L. Traber. 2006. The inhibition of inducible nitric oxide synthase in ovine sepsis model. Shock 25: 522-527.
Enkhbaatar, P., C. Joncam, L. Traber, Y. Nakano, J. Wang, M. Lange, R. Connelly, G. Kulp, F. Saunders, R. Huda, R. Cox, F. Schmalstieg, D. Herndon, and D. Traber. 2008. Novel ovine model of methicillin-resistant *Staphylococcus aureus*-induced pneumonia and sepsis. Shock 29: 642-649.
Sousse, L. E., C. C. Jonkam, D. L. Traber, H. K. Hawkins, S. W. Rehberg, L. D. Traber, D. N. Herndon, and P. Enkhbaatar. 2011. Pseudomonas aeruginosa is associated with increased lung cytokines and asymmetric dimethylarginine compared with methicillin-resistant *Staphylococcus aureus*. Shock 36: 466-470.
Enkhbaatar, P., C. Nelson, J. R. Salsbury, J. R. Carmical, K. E. Torres, D. Herndon, D. S. Prough, L. Luan, and E. R. Sherwood. 2015. Comparison of Gene Expression by Sheep and Human Blood Stimulated with the TLR4 Agonists Lipopolysaccharide and Monophosphoryl Lipid A. PLoS One 10: e0144345.
Enkhbaatar, P., A. Esechie, J. Wang, R. A. Cox, Y. Nakano, A. Hamahata, M. Lange, L. D. Traber, D. S. Prough, D. N. Herndon, and D. L. Traber. 2008. Combined anticoagulants ameliorate acute lung injury in sheep after burn and smoke inhalation. Clin Sci (Lond) 114: 321-329.
Cox, R. A., S. Jacob, G. Oliveras, K. Murakami, P. Enkhbaatar, L. Traber, F. C. Schmalstieg, D. N. Herndon, D. L. Traber, and H. K. Hawkins. 2009. Pulmonary expression of nitric oxide synthase isoforms in sheep with smoke inhalation and burn injury. Exp Lung Res 35: 104-118.
Lange, M., A. Hamahata, D. L. Traber, A. Esechie, C. Jonkam, K. Bansal, Y. Nakano, L. D. Traber, and P. Enkhbaatar. 2010. A murine model of sepsis following smoke inhalation injury. Biochem Biophys Res Commun 391: 1555-1560.
Jonkam, C. C., K. Bansal, D. L. Traber, A. Hamahata, M. O. Maybauer, D. M. Maybauer, R. A. Cox, M. Lange, R. L., Connelly, L. D. Traber, C. D. Djukom, J. R. Salsbury, D. N. Herndon, and P. Enkhbaatar. 2009. Pulmonary vascular permeability changes in an ovine model of methicillin-resistant *Staphylococcus aureus* sepsis. Crit Care 13: R19.
Bangham, A. D., Malcolm M. Standish, and Jeff C. Watkins. "Diffusion of univalent ions across the lamellae of swollen phospholipids." Journal of molecular biology 13.1 (1965): 238.

\* cited by examiner

A

B

PHOSPHORYLATED HEXAACYL DISACCHARIDES (PHADS) FOR TREATING OR PREVENTING INFECTIONS

CROSS REFERENCE TO RELATED APPLICATIONS

This application is a national stage application filed under 35 U.S.C. § 371 of PCT/US2018/030349 filed May 1, 2018, which claims the benefit of U.S. Provisional Patent Application Ser. No. 62/492,451 filed May 1, 2017, the disclosures of which are expressly incorporated herein by reference.

STATEMENT REGARDING FEDERALLY SPONSORED RESEARCH

This invention was made with Government Support under Grant No. RO1 GM104306 awarded by the National Institutes of Health. The Government has certain rights in the invention.

FIELD

The present disclosure relates to phosphorylated hexaacyl disaccharide (PHAD) compounds, compositions, and methods for treating or preventing infections.

BACKGROUND

Hospital-acquired infections, particularly those caused by antibiotic-resistant pathogens, are a major threat to public health affecting approximately two million patients and causing at least 90,000 deaths annually. Critically ill, immunosuppressed, and high-risk surgical patients are particularly vulnerable, although anyone receiving care in a modern health care facility is at risk. Patients that develop hospital-acquired infections have increased in-hospital morbidity and mortality and survivors show functional decline after leaving the hospital. Thus, strategies are needed to prevent the onset and decrease the severity of hospital-acquired infections.

Lipopolysaccharide (LPS, endotoxin) is the major natural TLR4 ligand. LPS is a component of the Gram-negative bacterial cell wall that has known immunomodulatory properties. LPS activates leukocytes, endothelial cells and some parenchymal cells by binding to toll-like receptor 4 (TLR4) and activating early host responses to infection. Recent studies show that mice primed with LPS have improved resistance to Gram negative and Gram positive bacterial infections and fungal infections.

Despite its effectiveness, the clinical application of lipopolysaccharide (LPS) is precluded by significant toxicity. However, derivatives of LPS have been developed that have markedly decreased toxicity and retain potent immunomodulatory activity. Among those agents is Monophosphoryl Lipid A (MPLA). MPLA is currently employed by Glaxo Smith Kline as a component of the FDA-approved ASO4 vaccine adjuvant system.

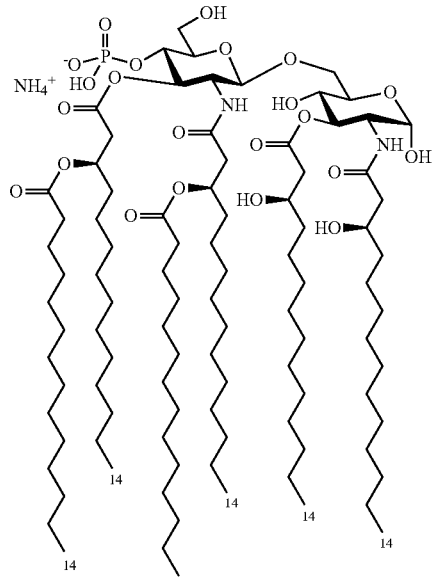

Monophosphoryl Lipid A (MPLA)

Unfortunately, MPLA is not available or suitable as a stand-alone immunotherapeutic. MPLA preparations are produced by hydrolysis of LPS from *Salmonella minnesota* resulting in a heterogeneous preparation. Furthermore, MPLA is currently only available as a component of a proprietary vaccine adjuvant system and not as a stand-alone immunotherapeutic. What is needed are synthetic lipopolysaccharides useful for treating bacterial and fungal infections.

The compounds, compositions, and methods disclosed herein address these and other needs.

SUMMARY

Disclosed herein are synthetic analogues of Monophosphoryl Lipid A (MPLA) having potent biological activity as prophylactic immunotherapeutic agents. The resultant phosphorylated hexaacyl disaccharides (PHADs) are structurally MPLA analogs that are synthesized de novo and have reproducible pharmacodynamics. The inventors have found that several PHAD variants (phosphorylated hexaacyl disaccharide (PHAD), 3-deacyl phosphorylated hexaacyl disaccharide (3D-PHAD), and 3-D (6-acyl) phosphorylated hexaacyl disaccharide (3D(6-acyl) PHAD)) are effective treatments for augmenting host resistance to bacterial infections.

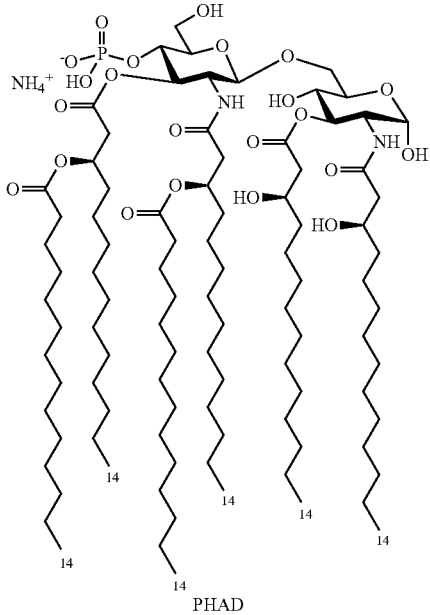

PHAD

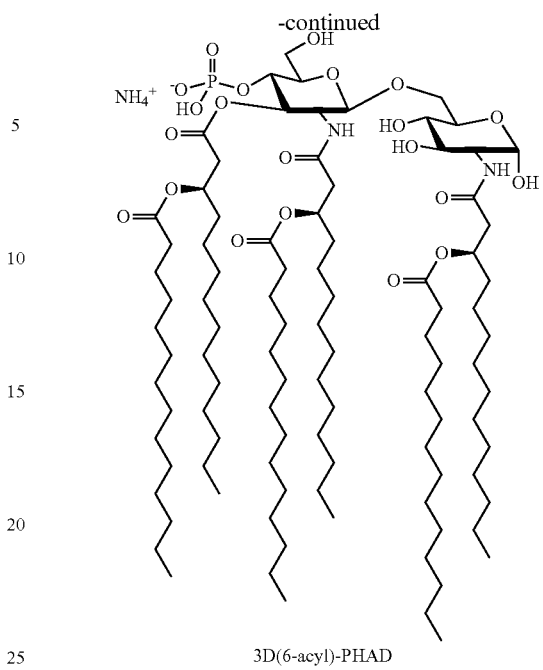

3D(6-acyl)-PHAD

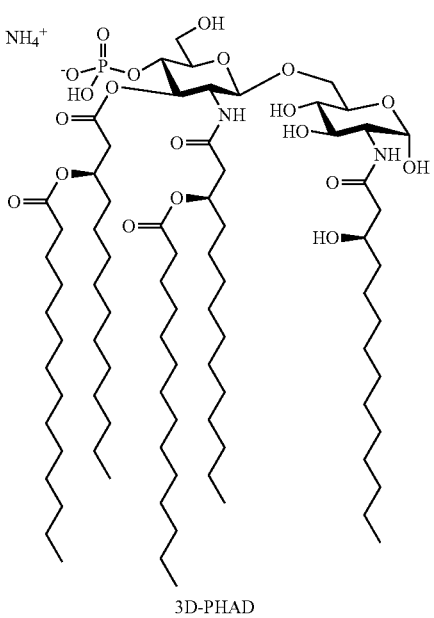

3D-PHAD

In one aspect, disclosed herein is a method for treating or preventing a bacterial infection or a fungal infection, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof.

In some embodiments, the compound is phosphorylated hexaacyl disaccharide (PHAD). In some embodiments, the compound is 3-deacyl phosphorylated hexaacyl disaccharide (3D-PHAD). In some embodiments, the compound is 3-D (6-acyl) phosphorylated hexaacyl disaccharide (3D(6-acyl) PHAD).

In some embodiments, the bacterial infection is a gram-negative bacteria. In some embodiments, the bacterial infection is a multi-drug resistant strain. In some embodiments, the bacterial infection is selected from *Pseudomonas aeruginosa* or *Staphylococcus aureus*.

In some embodiments, the fungal infection is *Candida albicans*.

In some embodiments, the subject is recovering from surgery. In some embodiments, the subject is recovering from trauma. In some embodiments, the trauma is a burn.

In another aspect, provided herein is a method for treating or preventing a bacterial infection or a fungal infection, comprising administering to a subject in need thereof an effective amount of a pharmaceutical composition comprising a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof, and a pharmaceutically acceptable carrier.

BRIEF DESCRIPTION OF THE DRAWINGS

The accompanying figures, which are incorporated in and constitute a part of this specification, illustrate several aspects described below.

DETAILED DESCRIPTION

Figure 1:
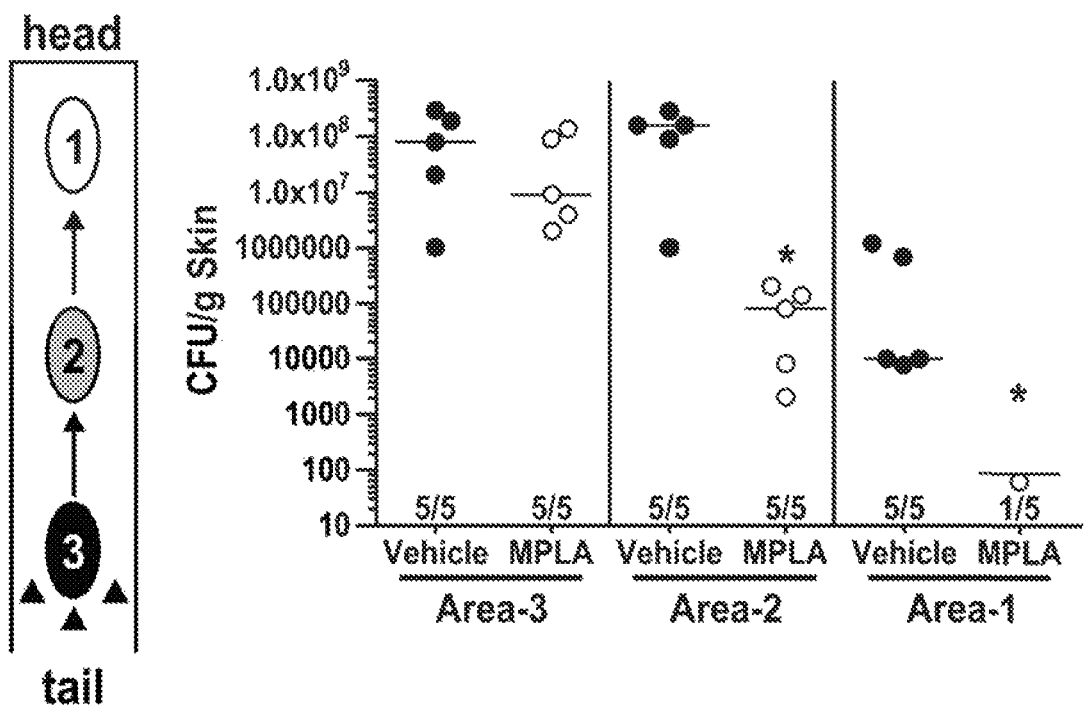
FIG. 1. MPLA treatment improves host resistance to *Pseudomonas* burn wound infection. Mice exposed to a 20% full thickness burn wound were treated with MPLA on days 3 and 4 post-burn and were inoculated with $1\times10^8$ *Pseudomonas aeruginosa* in the caudad (area 3) portion of the burn wound. A. Wounds were excised 48 hours after inoculation, sectioned into 3 segments (areas 1-3) and homogenized. Bacterial colony forming units (cfu) were determined by culture on agar plates. B. At 4-6 days after infection, wound and lungs were harvested, homogenized and cultured to measure *Pseudomonas* cfu. C. Survival was determined after *Pseudomonas* infection. *$p<0.05$ compared to vehicle.
Figure 1:
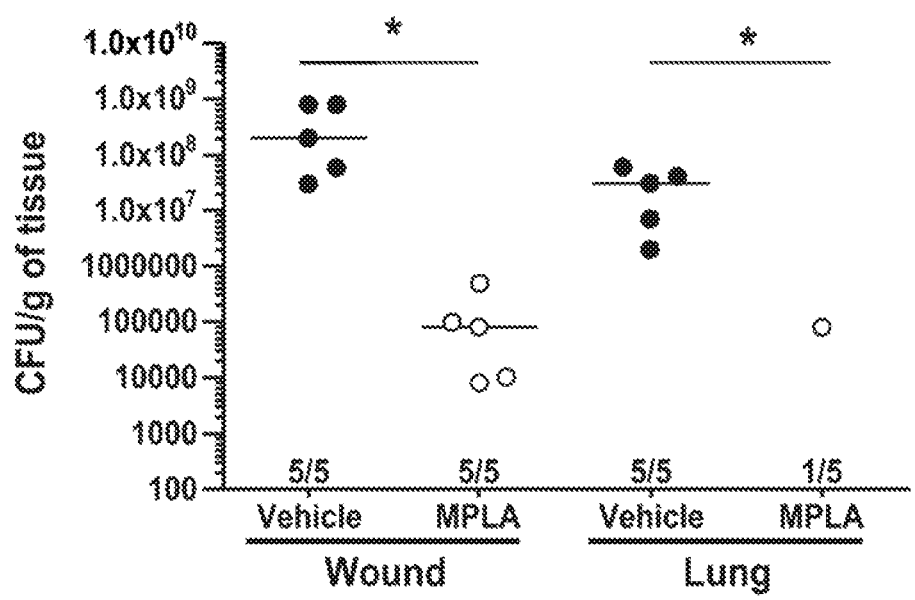
Figure 1:
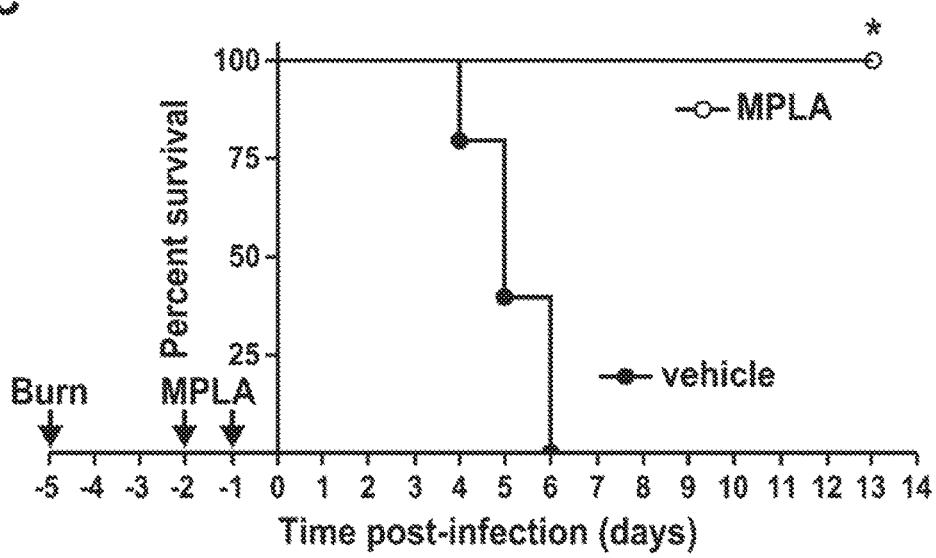

Disclosed herein are synthetic analogues of MPLA having potent biological activity as prophylactic immunotherapeutic agents. The resultant phosphorylated hexaacyl disaccharides (PHADs) are structurally MPLA analogs that are synthesized de novo and have reproducible pharmacodynamics. The inventors have found that several PHAD variants (phosphorylated hexaacyl disaccharide (PHAD), 3-deacyl phosphorylated hexaacyl disaccharide (3D-PHAD), and 3-D (6-acyl) phosphorylated hexaacyl disaccharide (3D(6-acyl) PHAD)) are effective treatments for augmenting host resistance to bacterial infection.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human. In some embodiments, the pharmacokinetic profiles of the systems of the present invention are similar for male and female subjects.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

Methods of Treatment

In one aspect, disclosed herein is a method for treating or preventing a bacterial infection or a fungal infection, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof.

In some embodiments, the compound is phosphorylated hexaacyl disaccharide (PHAD). In some embodiments, the compound is 3-deacyl phosphorylated hexaacyl disaccharide (3D-PHAD) (also sometimes referred to as Monophosphoryl 3-Deacyl Lipid A-Synthetic). In some embodiments, the compound is 3-D (6-acyl) phosphorylated hexaacyl disaccharide (3D(6-acyl) PHAD) (also sometimes referred to as Monophosphoryl Hexa-acyl Lipid A, 3-Deacyl-Synthetic). These synthetic lipids are all commercially available from Avanti Polar Lipids, Inc.

In one aspect, disclosed herein is a method for treating or preventing a bacterial infection or a fungal infection, comprising administering to a subject in need thereof an effective amount of a TLR4 agonist, or a pharmaceutically acceptable salt thereof.

In some embodiments, the TLR4 agonist is selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof. In some embodiments, the TLR4 agonist is a lipopolysaccharide (LPS), or derivatives or components of LPS. These TLR4 agonists can also include Monophosphoryl lipid A (MPLA). In some embodiments, the TLR4 agonist can be MPLA derived from *Salmonella minnesota*. These TLR4 agonists can also include aminoalkyl glucosaminide phosphates (AGPs). AGP compounds are known in the art and interact with TLR-4. AGPs include both acyclic and cyclic compounds (U.S. Pat. Nos. 6,113,918, and 6,303,347, WO 98/50399, WO 01/34617, WO 01/90129, and WO 02/12258, published Feb. 14, 2002; which are hereby incorporated by reference).

In some embodiments, the bacterial infection is a Gram-negative bacteria. In some embodiments, the bacterial infection is a multi-drug resistant strain. In some embodiments, the bacterial infection is selected from *Pseudomonas aeruginosa* or *Staphylococcus aureus*. In some embodiments, the bacterial infection is selected from *Pseudomonas aeruginosa*.

Examples of such Gram-negative bacteria include *Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens, Escherichia coli, Acinetobacter* spp. such as *Acinetobacter baumannii* or *Acinetobacter haemolyticus, Actinobacillus actinomycetemcomitans, Achromobacter* spp. such as *Achromobacter xylosoxidans* or *Achromobacter faecalis, Aeromonas* spp. such as *Aeromonas hydrophila, Bacteroides* spp. such as *Bacteroides fragilis, Bacteroides theataioatamicron, Bacteroides distasonis, Bacteroides ovatus* or *Bacteroides vulgatus, Bartonella* hensenae, *Bordetella* spp. such as *Bordetella pertussis, Borrelia* spp. such as *Borrelia Burgdorferi, Brucella* spp. such as *Brucella melitensis, Burkholderia* spp. such as *Burkholderia cepacia, Burkholderia pseudomallei* or *Burkholderia mallei, Campylobacter* spp. such as *Campylobacter jejuni, Campylobacter fetus* or *Campylobacter coli, Cedecea, Chlamydia* spp. such as *Chlamydia pneumoniae, Chlamydia trachomatis, Citrobacter* spp. such as *Citrobacter diversus* (*koseri*) or *Citrobacter freundii, Coxiella burnetii, Edwardsiella* spp. such as *Edwarsiella tarda, Ehrlichia chafeensis, Eikenella corrodens, Enterobacter* spp. such as *Enterobacter cloacae, Enterobacter aerogenes, Enterobacter agglomerans, Francisella tularensis, Fusobacterium* spp., *Haemophilus* spp. such as *Haemophilus influenzae* (beta-lactamase positive and negative) or *Haemophilus ducreyi, Helicobacter pylori, Kingella kingae, Klebsiella* spp. such as *Klebsiella oxytoca, Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella ozaenae, Legionella pneumophila, Mannheimia haemolyticus, Moraxella catarrhalis* (beta-lactamase positive and negative), *Morganella morganii, Neisseria* spp. such as *Neisseria gonorrhoeae* or *Neisseria meningitidis, Pasteurella* spp. such as *Pasteurella multocida, Plesiomonas shigelloides, Porphyromonas* spp. such as *Porphyromonas asaccharolytica, Prevotella* spp. such as *Prevotella corporis, Prevotella intermedia* or *Prevotella endodontalis, Proteus* spp. such as *Proteus mirabilis, Proteus vulgaris, Proteus penneri* or *Proteus myxofaciens, Porphyromonas asaccharolytica, Plesiomonas shigelloides, Providencia* spp. such as *Providencia stuartii, Providencia rettgeri* or *Providencia alcalhfaciens, Ricketsia prowazekii, Salmonella* spp. such as *Salmonella typhi* or *Salmonella paratyphi, Serratia marcescens, Shigella* spp. such as *Shigella flexneri, Shigella boydii, Shigella sonnei* or *Shigella dysenteriae, Streptobacillus moniliformis, Stenotrophomonas maltophilia, Treponema* spp., *Vibrio* spp. such as *Vibrio cholerae, Vibrio parahaemolyticus, Vibrio vulnmficus, Vibrio alginolyticus, Yersinia* spp. such as *Yersinia enterocolitica, Yersinia pestis* or *Yersinia pseudotuberculosis*.

In some embodiments, the bacterial infection is a Gram-positive bacteria. In some embodiments, the bacterial infection is *Staphylococcus aureus*.

Examples of Gram-positive bacteria include *Bacillus* spp., *Clostridium sporogenes, Lactobacillus* spp., *Lactococcus lactis, Leuconostoc mesenteroides, Listeria* spp., *Pediococcus cerevisiae, Staphylococcus aureus, Streptococcus agalactiae* or combinations thereof.

In another aspect, provided herein is a method for treating or preventing a bacterial infection or a fungal infection, comprising administering to a subject in need thereof an effective amount of a pharmaceutical composition comprising a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof, and a pharmaceutically acceptable carrier.

Although all critically ill patients are at risk of infection with antibiotic-resistant nosocomial pathogens, patients with major burns are among the most susceptible. The loss of the skin barrier, alterations in acquired and innate immune system functions and the use of invasive devices, such as central venous catheters and endotracheal tubes, predisposes burn victims to serious infections particularly with antibiotic resistant pathogens.

In some embodiments, the subject is recovering from surgery. In some embodiments, the subject is recovering from trauma. In some embodiments, the trauma is a burn.

In one aspect, disclosed herein is a method for treating or preventing an infection, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof.

In one aspect, disclosed herein is a method for treating or preventing an infection, comprising administering to a subject in need thereof an effective amount of a TLR4 agonist, or a pharmaceutically acceptable salt thereof.

In some embodiments, the infection is a bacterial infection. In some embodiments, the infection is a fungal infection.

The disclosed methods can in some embodiments be used to treat any fungal infection. In some embodiments, the disclosed methods can be used to treat a *Candida* spp. infection. In some embodiments, the disclosed methods can be used to treat a *C. albicans* infection.

In some embodiments, the fungal infection comprises *Candida auris*, aspergillosis, *Pneumocystis carinii* pneumonia (PCP), coccidioidomycosis (valley fever), cryptococcosis, histoplasmosis, or a combination thereof.

In one aspect, disclosed herein is a method for protecting organs in a high risk surgical subject or a critically ill subject, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof.

Additional Methods

MPLA and the synthetic PHADs disclosed herein are useful for a number of methods and indications, including for example, infection prophylaxis for serious burns, neutropenic fever in oncology prophylaxis, colon and rectal surgical wound infection prophylaxis, or for use in active therapy.

Infection Prophylaxis for Serious Burns

In one aspect, disclosed herein is a method for preventing infection in a subject with a burn injury, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof.

In 2016, there were an estimated 486,000 burn injuries receiving medical treatment. In addition, there were approximately 40,000 hospitalizations related to burn injury, including 30,000 at hospital burn centers. Over a twenty-year period, there was a 2.8% rate of death from pediatric burn unit admissions and 86% of those who died had a 40% or greater body surface area burn. Respiratory failure and sepsis are the leading causes of death in severely burned pediatric patients. Deficiencies or delays in resuscitation increase risk of death after burn despite the size of burn injury. Multi-organ failure is present in over 50% of all deaths after burn injury.

In one recent study, it was found that: (1) practically all pneumonias (95%) were endogenous, both primary and secondary; (2) more than half of the burn patients requiring mechanical ventilation (57%) developed a primary endogenous pneumonia at a median of 3 days; (3) the pneumonia rate was two times higher in the group with inhalation injury compared with the group without inhalation injury; (4) all but two primary endogenous pneumonias were caused by community-acquired bacteria, including *S. aureus*, *S. pneumoniae*, and *H. influenzae*; and (5) secondary endogenous pneumonias occurring at a median of 16 days were usually preceded by a primary endogenous pneumonia.

In another recent study, the epidemiological characteristics of burn patients developing pneumonia were determined, as well as the predisposing factors and the mortality of these patients. Infectious complications present serious problems in severely burned patients. Pneumonia, in particular, is a major cause of morbidity and mortality in burn patients. Patients with inhalation injuries are exposed to a greater risk due to the possible development of infectious complications in the lower respiratory tract. Risk factors for the development of pneumonia in burn patients were found to be inhalation trauma, high ABSI score, the Baux and modified Baux index, and high ASA score (p<0.01).

Neutropenic Fever in Oncology Prophylaxis

In one aspect, disclosed herein is a method for preventing neutropenic fever in a subject with cancer, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof.

Cancer patients receiving cytotoxic antineoplastic therapy sufficient to adversely affect myelopoiesis and the integrity of the gastrointestinal mucosa are at risk for invasive infection due to colonizing bacteria and/or fungi that translocate across intestinal mucosal surfaces. Since the magnitude of the neutrophil-mediated component of the inflammatory response may be muted in neutropenic patients, a fever may be the earliest and only sign of infection. It is critical to recognize neutropenic fever early and to initiate empiric systemic antibacterial therapy promptly in order to avoid progression to a sepsis syndrome and possibly death. Fever in neutropenic patients is defined as a single oral temperature of >38.3° C. (101° F.) or a temperature of >38.0° C. (100.4° F.) sustained for >1 hour. Severe neutropenia is usually defined as an absolute neutrophil count (ANC)<500 cells/microL or an ANC that is expected to decrease to <500 cells/microL over the next 48 hours. The risk of clinically important infection rises as the neutrophil count falls below 500 cells/microL.

It is crucial to assess the risk for serious complications in patients with neutropenic fever, since this assessment dictates the approach to therapy, including the need for inpatient admission, intravenous antibiotics, and prolonged hospitalization. Low-risk patients with neutropenic fever are those in whom the duration of neutropenia (ANC<500 cells/microL) is expected to be ≤7 days and those with no comorbidities or evidence of significant hepatic or renal dysfunction. Most patients receiving chemotherapy for solid tumors or lymphoma are considered to be low risk. High-risk patients with neutropenic fever as those who are expected to be neutropenic (ANC<500 cells/microL) for >7 days. Patients with neutropenic fever who have ongoing comorbidities or evidence of significant hepatic or renal dysfunction are also considered to be high risk, regardless of the duration of neutropenia. Profound prolonged neutropenia (ie, ANC≤100 cells/microL expected to last >7 days) is most likely to occur in the pre-engraftment phase of hematopoietic cell transplantation (HCT; particularly allogeneic) and in patients undergoing induction chemotherapy for acute leukemia.

An infectious source is identified in approximately 20 to 30 percent of febrile neutropenic episodes. Often the only evidence of infection is bacteremia, which is documented in 10 to 25 percent of patients. Approximately 80 percent of identified infections are believed to arise from the patient's endogenous flora. Gram-positive bacteria are the most common causes of infection in neutropenic patients, but gram-negative bacteria (eg, *Pseudomonas aeruginosa*) are generally associated with the most serious infections.

Colon and Rectal Surgical Wound Infection Prophylaxis

In one aspect, disclosed herein is a method for preventing infection in a subject, comprising administering to a subject in need thereof an effective amount of a compound selected from phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof; wherein the subject has undergone colon and/or rectal surgery.

There are a number of surgical patients who develop post-operative wound and surgical site infection. Thus, MPLA and PHADs are useful for treating the high incidence of post-operative wound infection for elective surgery, where a prophylactic treatment is to be given.

The rates of post-operative complications are approximately from 1-20% based on risk factors, and the rates are about 5-20% overall in various studies.

Active Therapy

In addition, MPLA and synthetic PHADs disclosed herein can be used as post-infection therapy. Thus, as described above, MPLA and synthetic PHADs can be used for both prophylaxis and for treatment of infections as well.

Combination Therapies

In one embodiment, a TLR4 agonist compound (for example, phosphorylated hexaacyl disaccharide (PHAD), 3-deacyl phosphorylated hexaacyl disaccharide (3D-PHAD), or 3-D (6-acyl) phosphorylated hexaacyl disaccharide (3D(6-acyl) PHAD)), or a pharmaceutically acceptable salt thereof, may be administered in combination with an additional antibiotic agent. In some embodiments, the TLR4 agonist enhances the effectiveness or activity of the additional antibiotic agent. In some embodiments, the combination of the TLR4 agonist and the additional antibiotic agent is synergistic.

Classes of antibiotics and representative constituents (antibiotic agents) thereof include, but are not limited to the aminoglycosides (e.g. amikacin, gentamicin, kanamycin, neomycin, netilmicin, streptomycin, tobramycin); the carbacephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasplazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

In some embodiments, the additional antibiotic agent is a broad-spectrum antibiotic. In some embodiments, the broad-spectrum antibiotic is imipenem/cilastatin (Primaxin).

In one embodiment, a TLR4 agonist (for example, phosphorylated hexaacyl disaccharide (PHAD), 3-deacyl phosphorylated hexaacyl disaccharide (3D-PHAD), or 3-D (6-acyl) phosphorylated hexaacyl disaccharide (3D(6-acyl) PHAD)), or a pharmaceutically acceptable salt thereof, may be administered in combination with an additional antifungal agent. In some embodiments, the TLR4 agonist enhances the effectiveness or activity of the additional antifungal agent. In some embodiments, the combination of the TLR4 agonist and the additional antifungal agent is synergistic.

In some embodiments, the additional antifungal agent is selected from amphotericin B, flucytosine, imidazoles, triazoles, ketoconazole, itraconazole, fluconazole, terbinafine, butoconazole, ciclopirox olamine, haloprogin, tolnaftate, naftifine, butenafine, echinocandin B, a polyene antifungal antibiotic, undecylenic acid, benzoic acid, salicylic acid, propionic acid, caprylic acid, or potassium iodide.

Compositions

Compositions, as described herein, comprising an active compound (for example, phosphorylated hexaacyl disaccharide (PHAD), 3-deacyl phosphorylated hexaacyl disaccharide (3D-PHAD), or 3-D (6-acyl) phosphorylated hexaacyl disaccharide (3D(6-acyl) PHAD)) and an excipient of some sort may be useful in a variety of applications.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005). The pharmaceutically acceptable excipients may also include one or more of fillers, binders, lubricants, glidants, disintegrants, and the like.

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

In one embodiment, the pharmaceutical composition is delivered in an aqueous solution. In one embodiment, the pharmaceutical composition is delivered in a triethylamine solution. In one embodiment, the pharmaceutical composition is delivered in a 0.2% triethylamine solution.

In one embodiment, the pharmaceutical composition is in the form of a liposome or other slow release mechanism. Non-limiting examples are described in U.S. Pat. No. 5,888,519 (which is hereby incorporated by reference for such teaching) and include polymers of various types, microcapsules, and microspheres.

In some embodiments, methods for making liposome preparations are described by Bangham (Bangham et. al, 1965, J. Mol. Biol., 13, pp. 238-252). This preparation involves dissolving phospholipids in an organic solvent which is then evaporated to dryness leaving a thin lipid film on the inside of the test tube. The dry lipid film is then hydrated in an appropriate amount of aqueous phase and the mixture is heated to above the phase transition temperature of the lipids and allowed to "swell". The resulting liposomes which consist of multilamellar vesicles (MLV's) are dispersed by shaking the test tube. The lipids constituting the vesicular bilayer membranes are organized such that the hydrophobic hydrocarbon "tails" are oriented toward the center of the bilayer while the hydrophilic "heads" orient towards the in- and outside aqueous phase, respectively. This preparation provides the basis for producing unilamellar vesicles (UV) by methods such as sonication or extrusion as described by U.S. Pat. Nos. 4,235,871 and 5,008,050 (each of the foregoing are hereby incorporated by reference for such teaching).

Liposomes are ordinarily understood to comprise of lipid membranes that are capable of enclosing an internal aqueous space and the membranes may consist of a variety of types of lipids. Among the lipids that have been used either alone or in combination with other lipids to construct liposomes are, for example, phospholipids, glycolipids, glycophospholipids, diglycerides, triglycerides, sterols, steroids, terpenoids, and free fatty acids.

In some embodiments, liposomes for use in the pharmaceutical formulations of the present disclosure comprise a mixture of dimyristoyl phosphatidylcholine (DMPC), dimyristoyl phosphatidyl glycerol (DMPG), and cholesterol (Chol). The compounds of the present disclosure may be incorporated into such liposomes as is known in the art (see for example. PCT publication numbers WO2007/068411 and WO2005/081872 which are hereby incorporated by reference herein for such teachings) and described herein.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Toll-Like Receptor 4 (TLR4) Agonists Phosphorylated Hexaacyl Disaccharide (PHAD), 3-Deacyl Phosphorylated Hexaacyl Disaccharide (3D-PHAD), and 3-D (6-Acyl) Phosphorylated Hexaacyl Disaccharide (3D-PHAD) for Treating Infection with Antibiotic-Resistant Pathogens Infection with antibiotic resistant pathogens is one of the great modern threats to public health in Western nations. While efforts are underway to develop new antibiotics, currently no breakthroughs are on the horizon. New strategies are needed to prevent the onset and decrease the severity of infections. Immunotherapy provides a means of achieving that goal. In this example, the toll-like receptor 4 (TLR4) agonists phosphorylated hexaacyl disaccharide (PHAD), 3-deacyl phosphorylated hexaacyl disaccharide (3D-PHAD), and 3-D (6-acyl) phosphorylated hexaacyl disaccharide (3D(6-acyl) PHAD) are used as a prophylactic immunotherapeutic drug that augments host resistance against common nosocomial pathogens having high rates of antibiotic resistance.

Experiments focus on three prevalent nosocomial pathogens having high rates of antibiotic resistance, all classified by the CDC as "Serious" threats to public health: *Pseudomonas aeruginosa, Staphylococcus aureus* and *Candida albicans*. Although this example targets antibiotic-resistant, nosocomial pathogens, immunotherapy has broad potential to provide non-specific resistance to numerous emerging pathogens and to augment the efficacy of existing antibiotics.

This example shows that treatment with the toll-like receptor 4 (TLR4) agonist monophosphoryl lipid A (MPLA) can potently and non-specifically enhance resistance to infection with *P. aeruginosa, S. aureus*, and *C. albicans*. A partially dephosphorylated variant of native lipid A, MPLA is currently part of an FDA-approved adjuvant system marketed by GlaxoSmithKline. However, MPLA is a heterogeneous natural product not optimized for use as a stand-alone immunotherapeutic. To address that shortcoming, several pure synthetic analogues of MPLA having potent biological activity were examined as prophylactic immunotherapeutic agents. The resultant phosphorylated hexaacyl disaccharides (PHADs) are structurally uniform MPLA analogs that are synthesized de novo and have reproducible pharmacodynamics. These results show that three PHAD variants (phosphorylated hexaacyl disaccharide (PHAD), 3-deacyl phosphorylated hexaacyl disaccharide (3D-PHAD), and 3-D (6-acyl) phosphorylated hexaacyl disaccharide (3D(6-acyl) PHAD)) are as effective as MPLA at augmenting host resistance to bacterial infection.

Nosocomial infections represent a highly prevalent, and potentially preventable, cause of prolonged hospitalization, poor functional outcome and death in critically ill and other hospitalized patients (5-7). The emergence of antibiotic resistance among nosocomial pathogens has worsened the situation to "crisis" proportions (8). As noted in one commentary, "a complete overhaul of the approaches to resistance, disease and prevention could change the continuing upward trajectory of antibiotic resistant infections" (8). Although all critically ill patients are at risk of infection with antibiotic-resistant nosocomial pathogens, patients with major burns are among the most susceptible. The loss of the skin barrier, alterations in acquired and innate immune system functions and the use of invasive devices, such as central venous catheters and endotracheal tubes, predisposes burn victims to serious infections particularly with antibiotic resistant pathogens (4, 9-11). In a cohort of pediatric burn patients, Williams et al showed that 47% of mortality was due to sepsis and that 73% of septic patients were infected with antibiotic resistant organisms (4). *Pseudomonas aeruginosa* was responsible for 64% of deaths caused by antibiotic resistant bacteria in their cohort.

Bacterial lipopolysaccharide (LPS, endotoxin) is a component of the Gram negative bacterial cell wall that has known immunomodulatory properties. LPS activates leukocytes, endothelial cells and some parenchymal cells by binding to toll-like receptor 4 (TLR4) and activating early host responses to infection (12, 13). Recent studies show that mice primed with LPS have improved resistance to Gram negative and Gram positive bacterial infections (14-17). The augmented resistance to infection is associated with enhanced neutrophil-mediated anti-microbial functions, attenuation of pro-inflammatory cytokine production and modulation of the metabolic response of macrophages and monocytes to infection (18-21). Neutrophils from mice primed with LPS possess enhanced phagocytic and bacterial killing functions, all of which are associated with improved bacterial clearance and survival during infection (18, 21).

Despite its effectiveness, the clinical application of LPS is precluded by significant toxicity (22, 23). However, derivatives of LPS have been developed that have markedly decreased toxicity and retain potent immunomodulatory activity. Among those agents is Monophosphoryl Lipid A (MPLA) (18, 24). MPLA is produced by hydrolytic removal of the C1 phosphate group from the diphosphoryl lipid A moiety of LPS (25). That structural alteration decreases toxicity such that doses of MPLA that are 1000-10,000 times greater than LPS can be administered to humans before adverse side effects occur (26).

Figure 2:
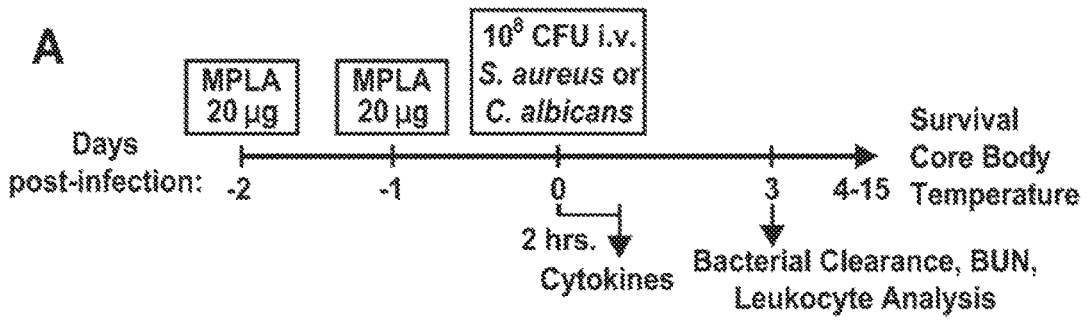
FIG. 2. MPLA induces resistance to *S. aureus* and *C. albicans* infection. A) WT BALB/c mice were injected with intravenous MPLA (20 μg/mouse) or vehicle one and two days prior to intravenous inoculation with intravenous $10^8$ cfu *S. aureus* or $10^8$ cfu *C. albicans*. B) Kaplan Meier survival curve of vehicle- and MPLA-primed mice. (n=12 mice/group) after *S. aureus* inoculation. C) Core (rectal) body temperature assessed daily after *S. aureus* inoculation. D) *S. aureus* cfu per gram of tissue recoverable from whole spleen, lung, and kidney in vehicle and MPLA-primed mice at 3 days after *S. aureus* inoculation. E) Concentration of serum IL-6 2 hours after *S. aureus* inoculation or vehicle. F) Concentration of serum BUN 3 days after *S. aureus* inoculation or vehicle. G) Kaplan Meier survival curve of vehicle- and MPLA-primed mice. (n=12 mice/group) after intravenous $10^8$ cfu *C. albicans* inoculation. H) Core (rectal) body temperature after *C. albicans* inoculation. Data shown as mean+/−SEM. For Kaplan-Meier plots *, $p<0.05$ via log-rank Mantel-Cox test. Otherwise, *, $p<0.05$ as determined by ANOVA with Tukey's post-hoc multiple comparison test.
Figure 2:
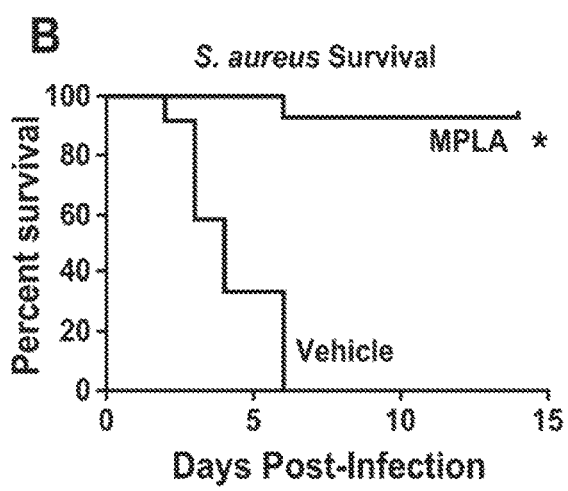
Figure 2:
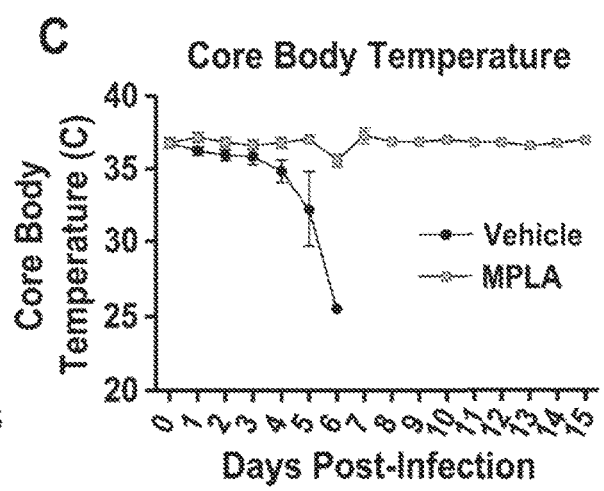
Figure 2:
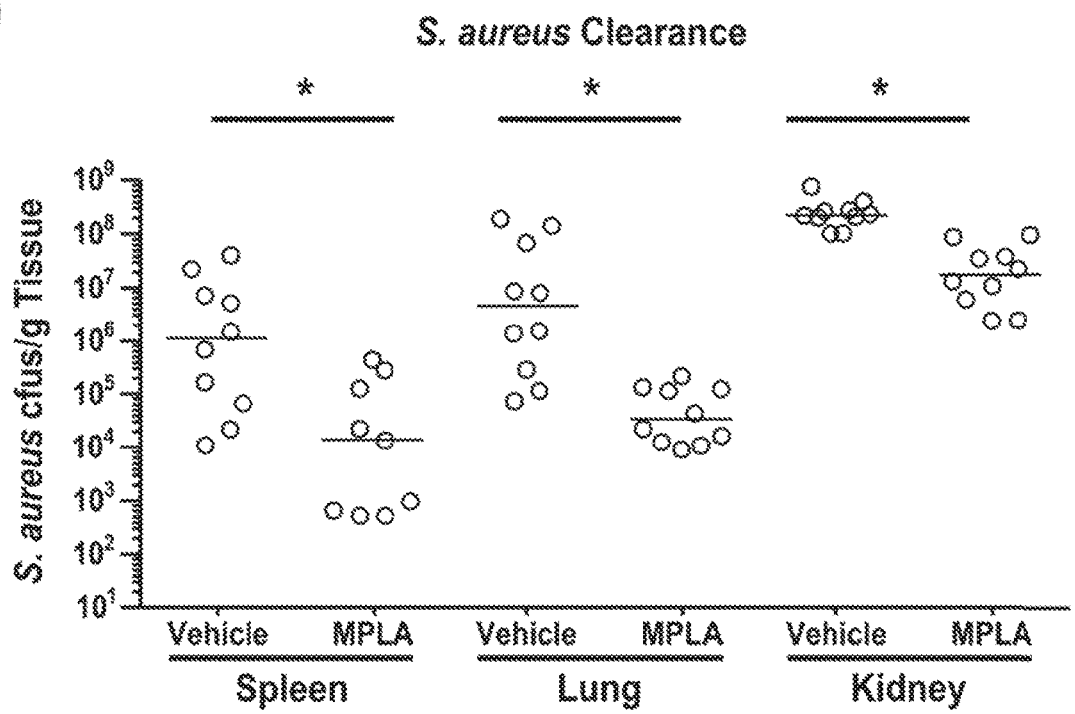
Figure 2:
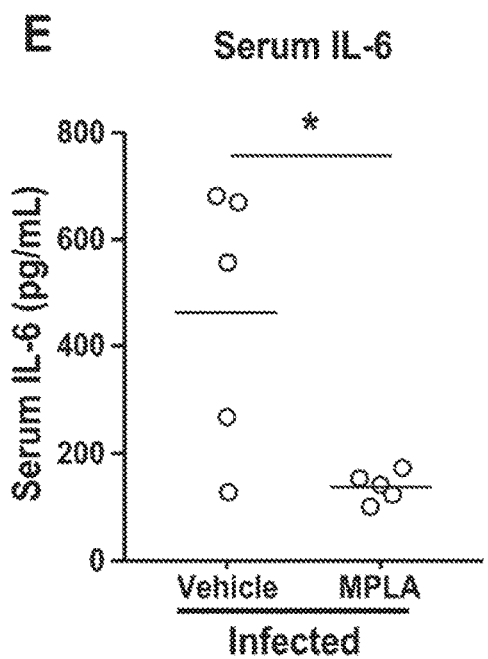
Figure 2:
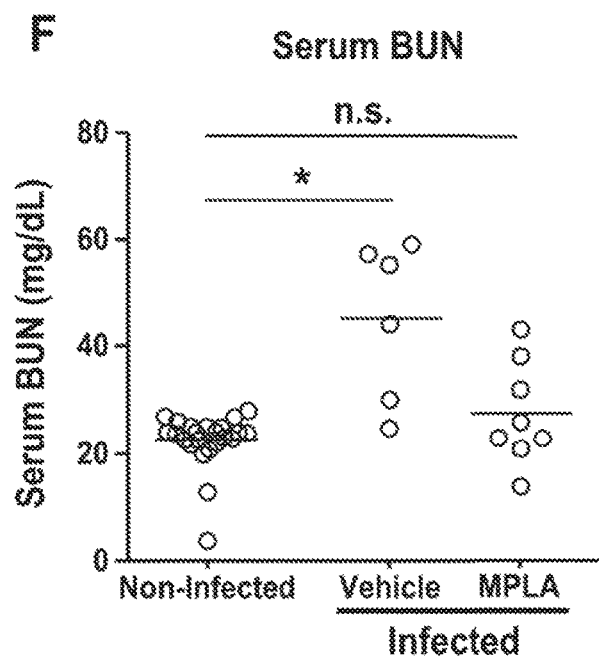
Figure 2:
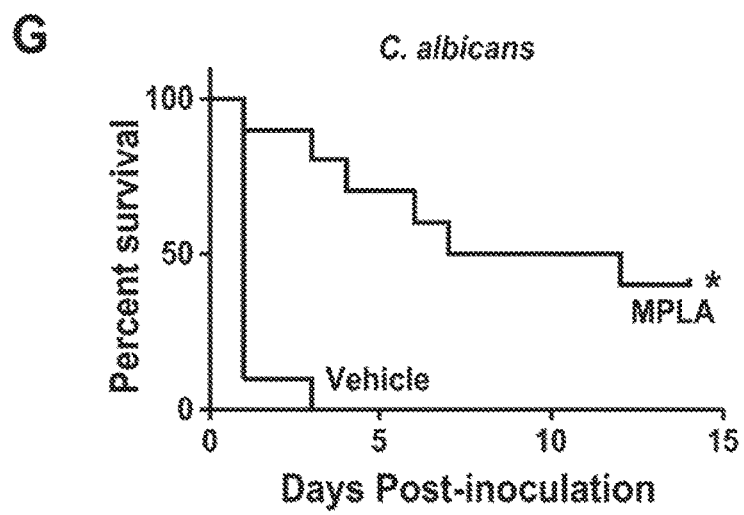
Figure 2:
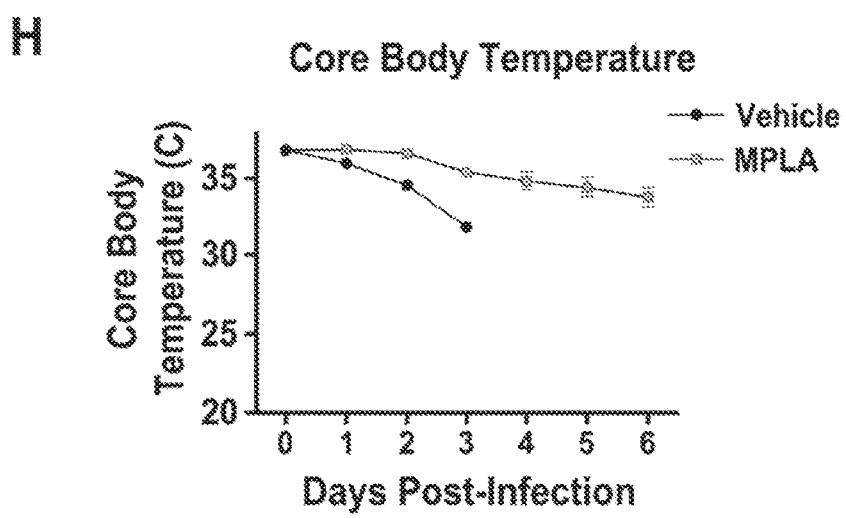

Consequently, MPLA is currently employed by Glaxo Smith Kline as a component of the FDA-approved ASO4 vaccine adjuvant system (27, 28). This example shows that MPLA improves innate host resistance to *Pseudomonas aeruginosa* burn wound infection as well as systemic infection with *S. aureus* or *C. albicans* (18)(FIGS. 1 and 2). Mice treated with MPLA (20 µg) beginning 2 days after a 20% cutaneous burn and infected with *Pseudomonas aeruginosa* at the wound site (area 3) on day 5 post-burn showed decreased spread of bacteria within the burn wound (areas 1 and 2, FIG. 1A). It was also shown that total wound bacteria and dissemination of *Pseudomonas* from the burn wound to the lungs was diminished in mice treated with MPLA (FIG. 1B). One hundred percent survival was observed in mice treated with MPLA whereas all mice in the vehicle-treated group died (FIG. 1C).

Figure 9:
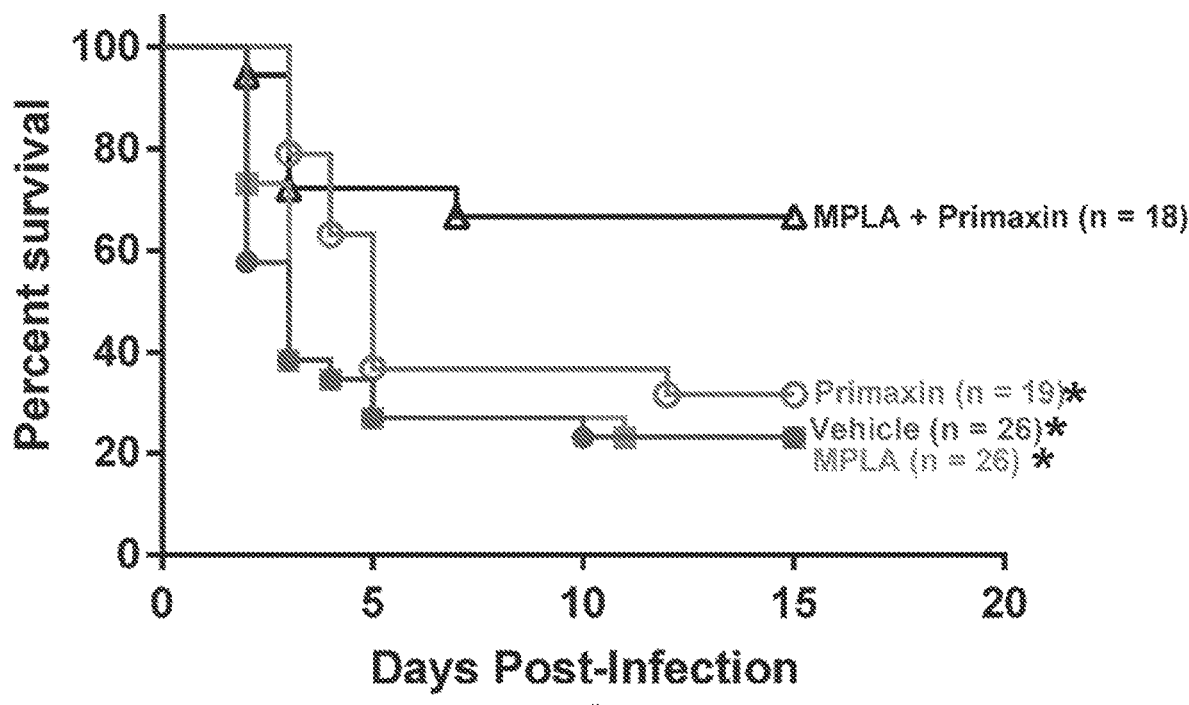
FIG. 9. The combination of MPLA and Primaxin improves survival when administered after the onset of *Pseudomonas* wound infection. Mice received a 20% TBSA burn followed by inoculation of the burn wound with *P. aeruginosa* ($1\times10^8$) 4 days later. Treatment with MPLA (20 μg) and/or Primaxin (25 mg/kg) was initiated at 24 and 48 hours after initiation of burn wound infection. Survival was monitored for 2 weeks. N=18-26 mice/group and represents combination of four separate runs. *$p<0.05$ compared to MPLA plus Primaxin.

The efficacy of MPLA was examined in combination with the broad spectrum antibiotic imipenem/cilastatin (Primaxin), when administered 24 hours after *P. aeruginosa* burn wound infection (FIG. 9). Mice treated only with vehicle, MPLA or Primaxin showed 60-75% mortality with no significant differences among groups. The combination of MPLA and Primaxin significantly improved survival and decreased mortality to 25%, which was significantly better than all other treatments (FIG. 9). These studies indicate that MPLA augments the efficacy of Primaxin against an antibiotic resistant strain of *P. aeruginosa*. This finding has major implications for the care of critically ill patients, particularly those infected with antibiotic resistant pathogens.

MPLA is also effective in improving survival in models of systemic *S. aureus* and *C. albicans* infection. Mice treated with MPLA (20 µg) after a 20% cutaneous burn received intravenous challenge with *S. aureus* or *C. albicans* ($1\times10^8$ CFU) on day 5 post-burn (FIG. 2). During *S. aureus* infection, MPLA-treated mice showed 90% survival compared to 14% in vehicle-treated mice (FIG. 2B). MPLA treatment also improved survival during *C. albicans* infection (40% vs 0%) compared to vehicle-treated controls (FIG. 2G). The improvement in survival was associated with improved bacterial clearance, lower plasma cytokine concentrations, less kidney injury and attenuated infection-induced hypothermia, indicating preserved physiologic integrity (FIG. 2, C-F, H). These results show that treatment with MPLA augments host resistance to diverse pathogens that are common causes of nosocomial infection.

Figure 10:
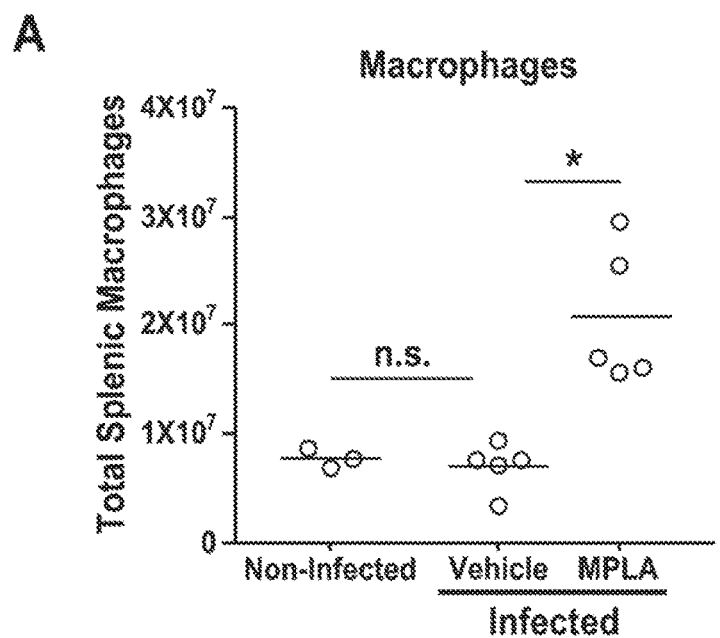
FIG. 10. MPLA induces resistance to infection via modulation of tissue macrophages and neutrophils. A-C) Total splenic A) macrophages, B) neutrophils, and C) monocytes 3 days after *S. aureus* inoculation or vehicle in MPLA- and vehicle-primed mice. D) Representative image of F4/80$^+$ immunohistochemical staining (brown) in kidney 3 days after *S. aureus* inoculation in MPLA- and vehicle-primed mice E) Optical density quantification of F4/80$^+$ staining in kidneys. F) Mice were primed with MPLA or vehicle via intraperitoneal injection and 24 hours later pHrodo tagged *S. aureus* bioparticles were injected into the peritoneal cavity. Peritoneal leukocytes were harvested 6 hours later and assessed for pHrodo MFI via flow cytometry. G) Mice were primed with MPLA or vehicle via intraperitoneal injection and 24 hours later leukocytes were harvested from the peritoneal cavity. Respiratory burst was elicited by 45 minutes of PMA stimulation and DHR 123 MFI of macrophages, neutrophils, and monocytes was assessed by flow cytometry. H) Mice were administered intravenous clodronate-liposomes 24 hours prior to the first MPLA administration. Mice were then inoculated with intravenous $10^8$ cfu *S. aureus*. Kaplan-Meier survival plot after *S. aureus* infection (n=15 mice/group). I) Mice were administered intravenous anti-Ly6G antibody 24 hours prior to the first MPLA administration. Mice were then inoculated with intravenous $10^8$ cfu *S. aureus*. Kaplan-Meier survival plot after *S. aureus* infection (n=10 mice/group). J) C57BL6 WT and CCR2$^{-/-}$ mice were primed with MPLA or vehicle and inoculated with intravenous $10^8$ cfu *S. aureus*. Kaplan-Meier survival plot after *S. aureus* infection (n=10 mice/group). K) WT C57BL6 and RAG2$^{-/-}$ mice were injected with intravenous MPLA or vehicle prior to intravenous inoculation with $10^8$ cfu *S. aureus*. Kaplan-Meier survival plot (n=10 mice/group). Data shown as mean+/−SEM. For Kaplan-Meier plots *, p<0.05 via log-rank Mantel-Cox test. Otherwise, *, p<0.05 as determined by ANOVA with Tukey's post-hoc multiple comparison test FIG. 11. MPLA drives persistent and dynamic metabolic reprogramming in macrophages. A) Bone marrow derived macrophages (BMDMs) were primed with 1 µg/mL MPLA for 24 hours, washed, and rested for 3 days (3 dp macrophages). These macrophages were compared to BMDMs stimulated with 1 µg/mL MPLA for 24 hours prior to assessment (24 hr macrophages) and untreated BMDMs (control). B) Glycolysis stress test of macrophages as determined by the Seahorse Xf°96. C) Maximal extracellular acidification rate (ECAR) derived after the addition of oligomycin in the glycolysis stress test D) Glucose consumed from BMDMs over 24 hours, as determined by glucose concentration in cell-free medium subtracted by cell-containing medium. E) Lactate produced by BMDMs over 24 hours, as determined by lactate in cell-containing medium subtracted by cell free medium. F) Basal oxygen consumption rate (OCR) determined after the addition of glucose in the glycolysis stress test. G) Mitochondrial stress test of BMDMs as determined by the Seahorse Xfi96. H) Maximal oxidative rate derived after the addition of FCCP in the mitochondrial stress test. I) Intracellular ATP from BMDMs as determined by luminescence assay. Some BMDMs were exposed to 10 mM 2-DG or IlpM oligomycin for 3 hours prior to the assay. J) MitoTracker Green staining of BMDMs as determined by flow cytometry. K) Mitochondrial DNA (mtDNA)/nuclear DNA (nucDNA) as determined by qPCR. L) Succinate dehydrogenase (SDHA), citrate synthase (CS), and β-actin as determined by western blot. All bands shown derived from the same samples. Blot cropped to demonstrate relevant bands. Densitometry of SDHA and CS compared to β-actin derived from ImageJ shown. All experiments replicated at least twice. Data shown as mean+/−SEM. *, p<0.05 as determined by ANOVA with Tukey's post-hoc multiple comparison analysis.
Figure 10:
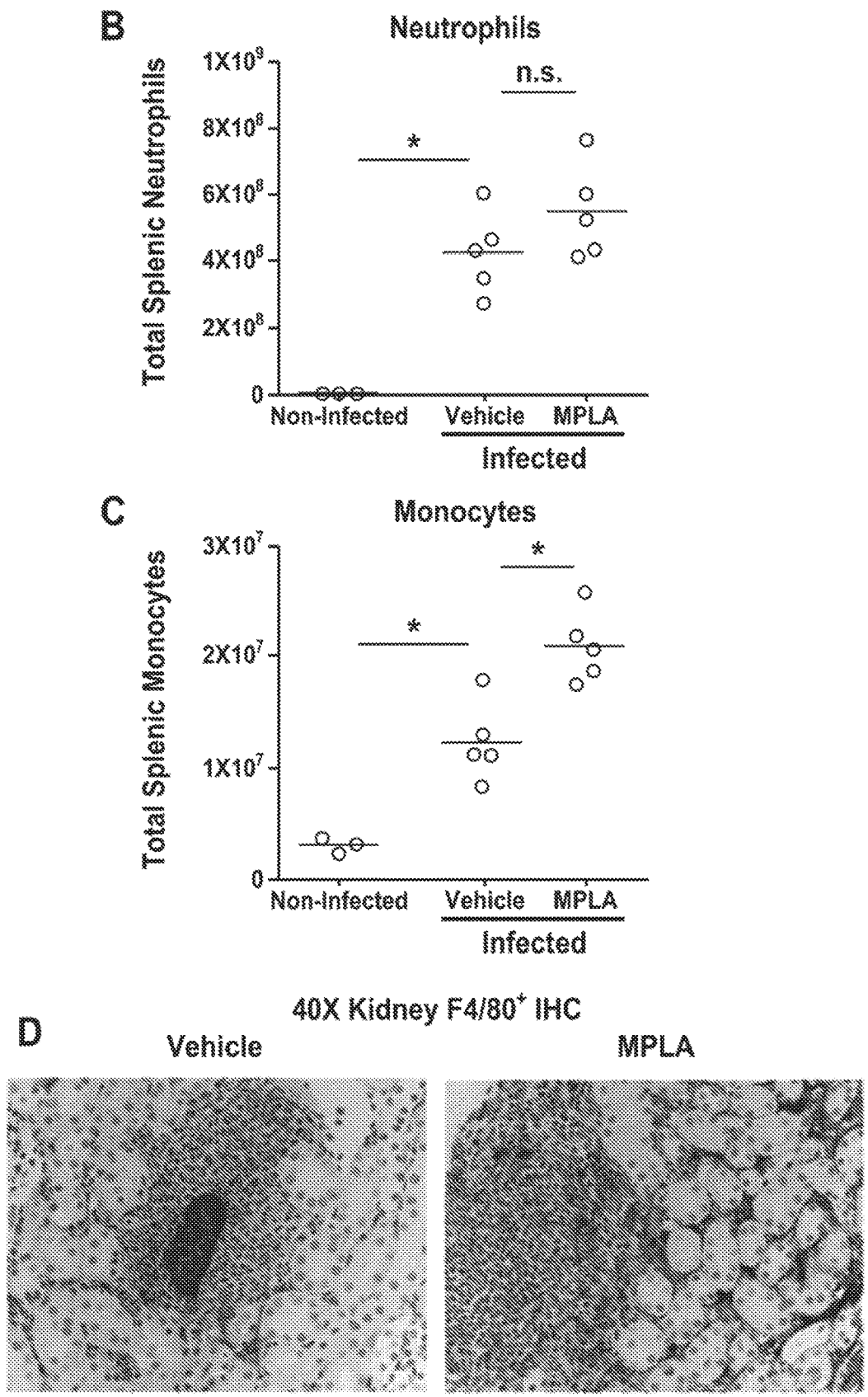
Figure 10:
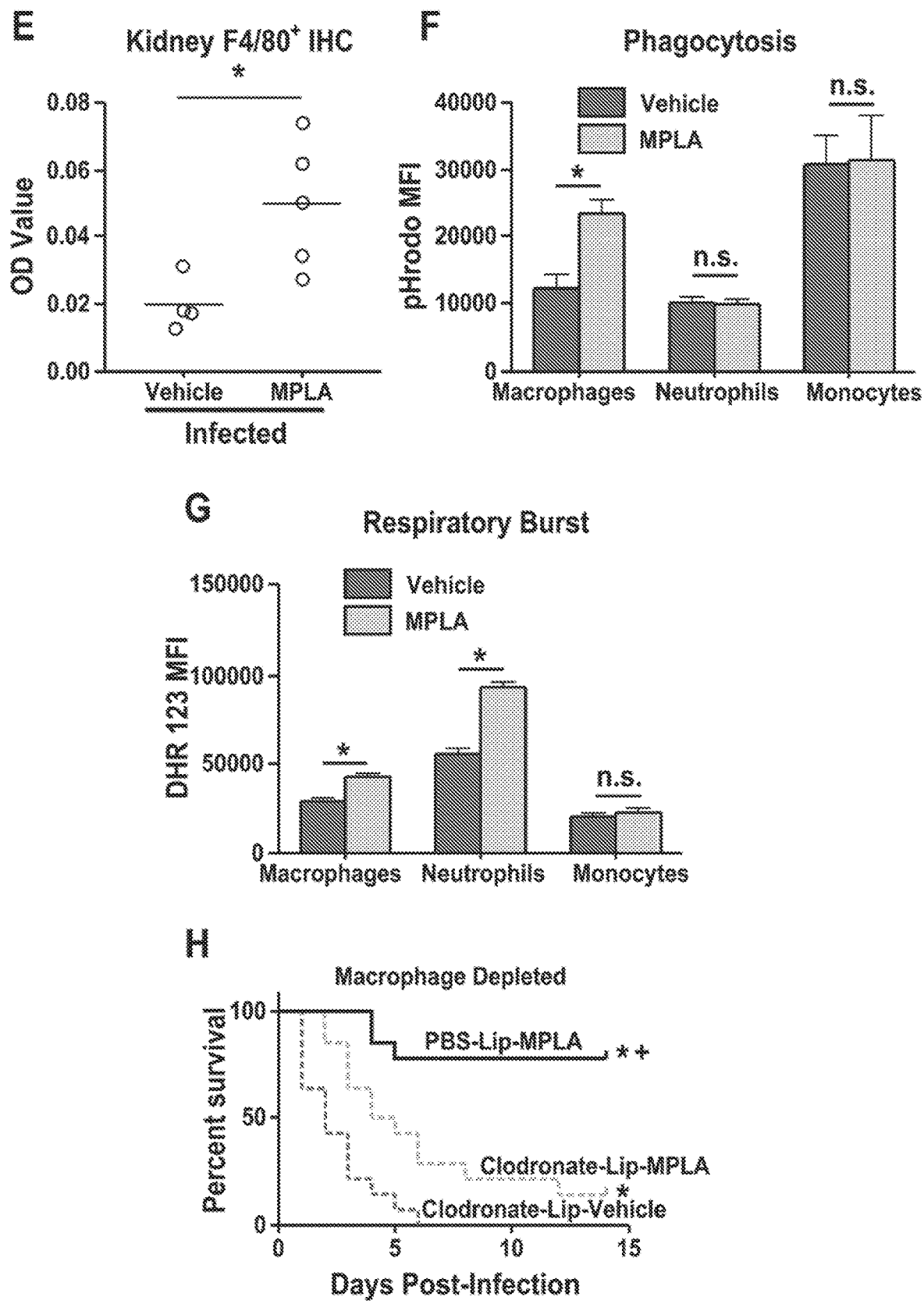
Figure 10:
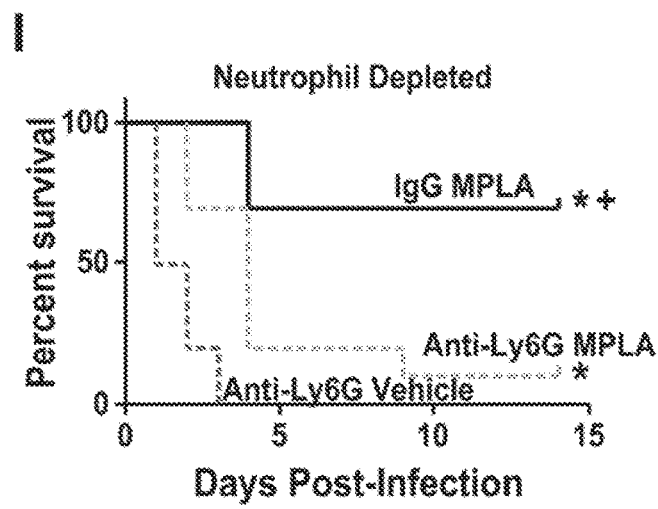
Figure 10:
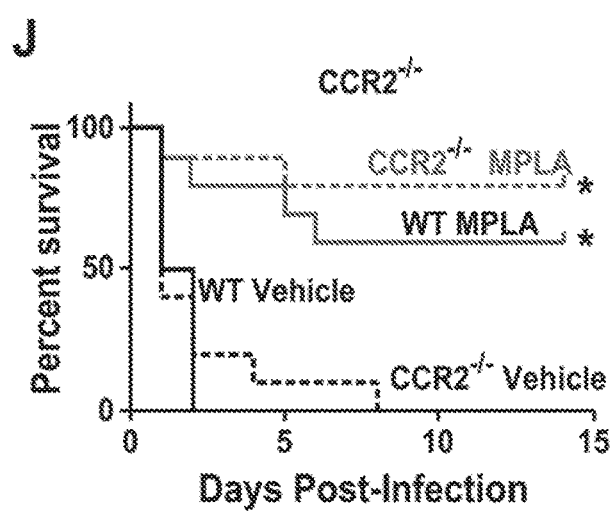
Figure 10:
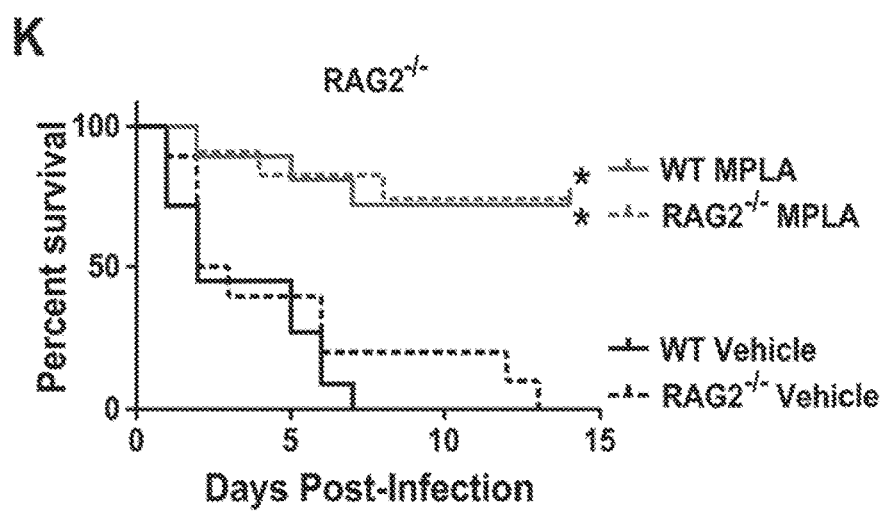

As shown in FIG. 10, MPLA induces resistance to infection via modulation of tissue macrophages and neutrophils. MPLA treatment increases macrophage, monocyte and neutrophil accumulation in the spleen (FIG. 10, A-C), increases macrophage accumulation in *S. aureus* abscesses (FIG. 10, D-E) and increases macrophage phagocytosis and respiratory burst functions (FIG. 10, F-G). Depletion of macrophages or neutrophils, but not cells of the adaptive immune system, ablates the beneficial effects of MPLA (FIG. 10, H-K).

Figure 11:
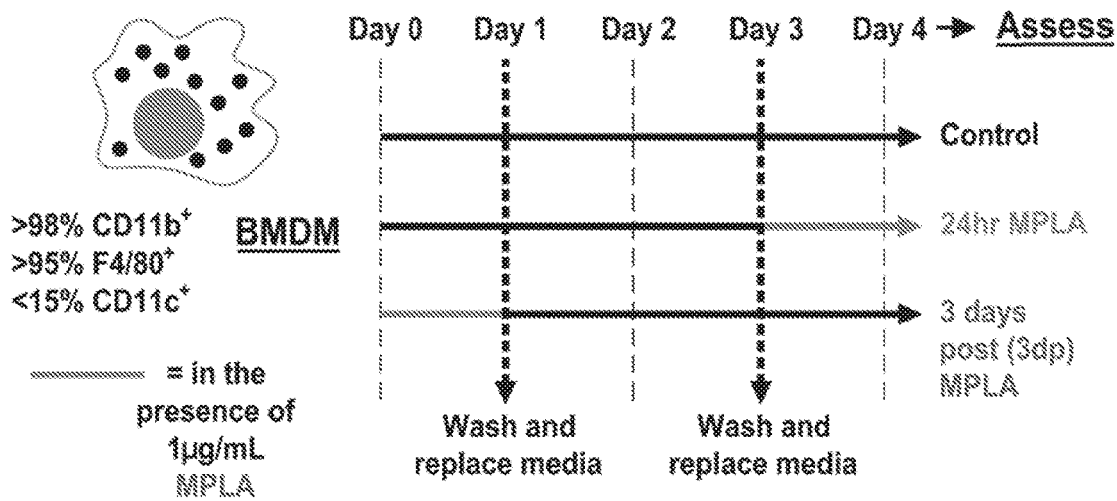
Figure 11:
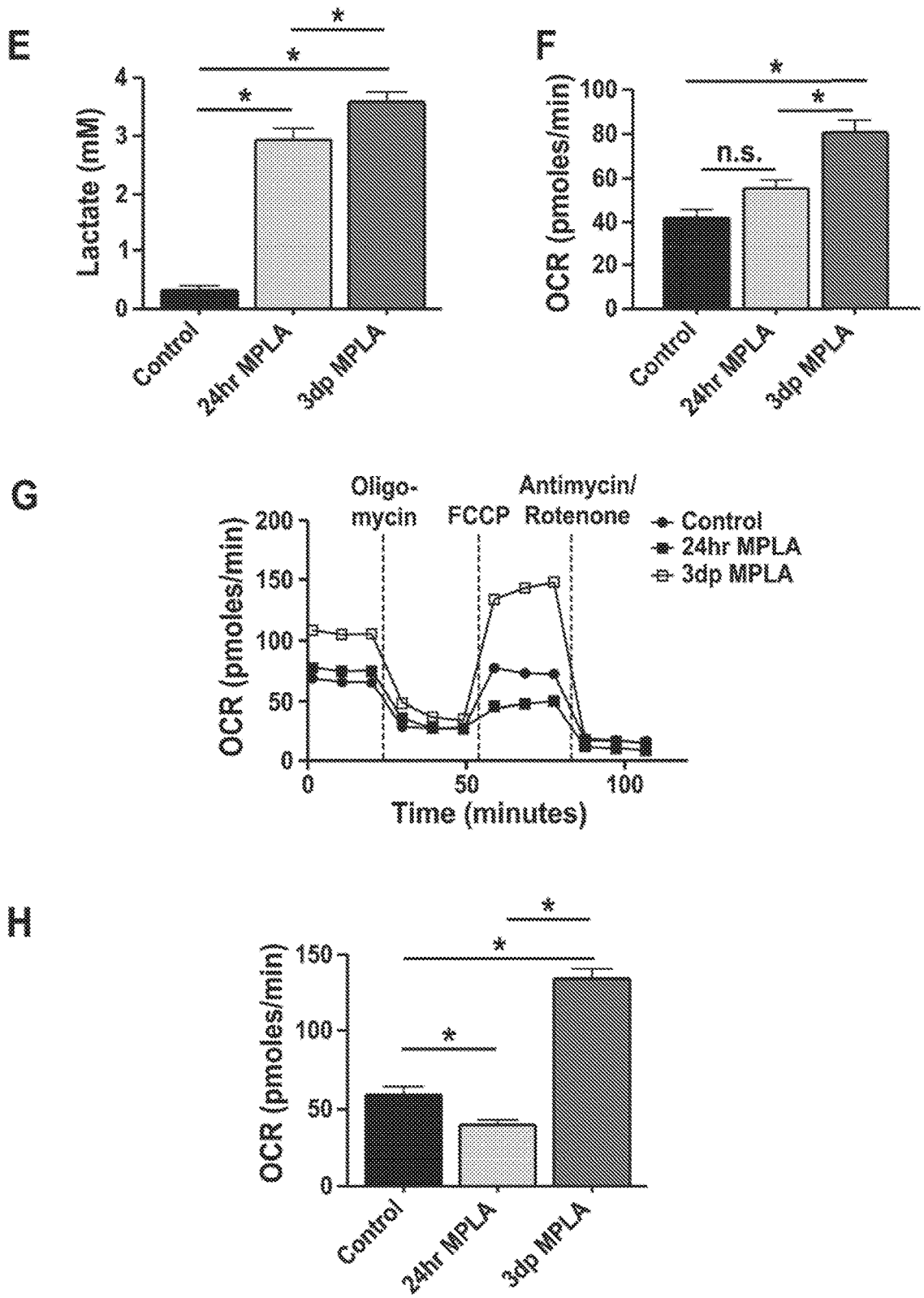
Figure 11:
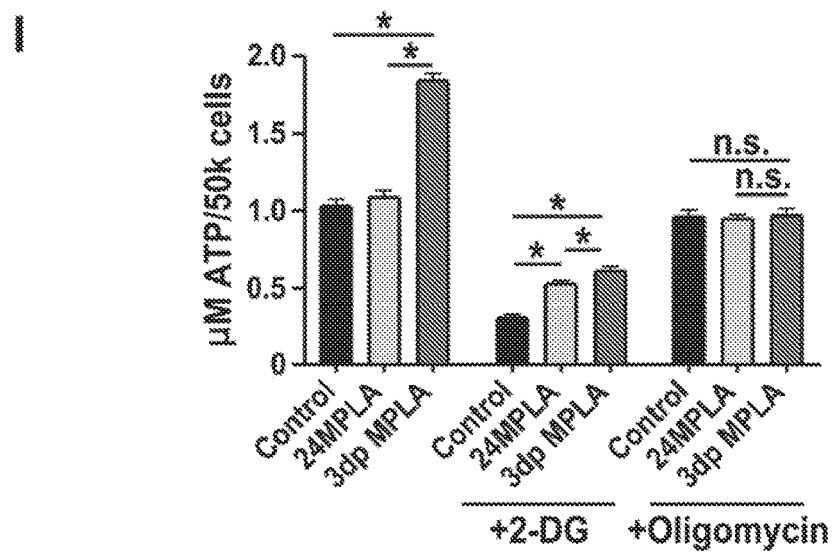
Figure 11:
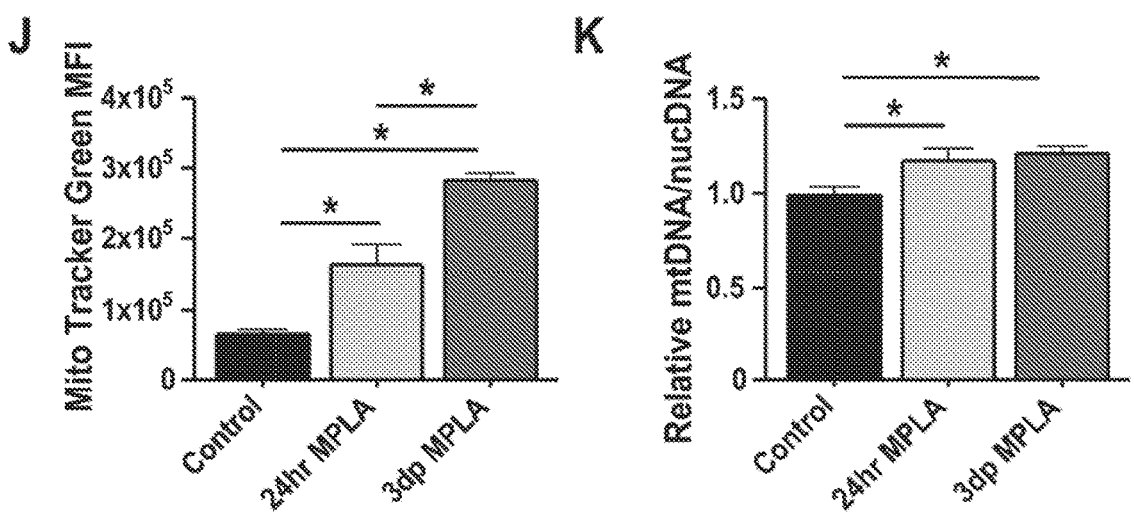
Figure 11:
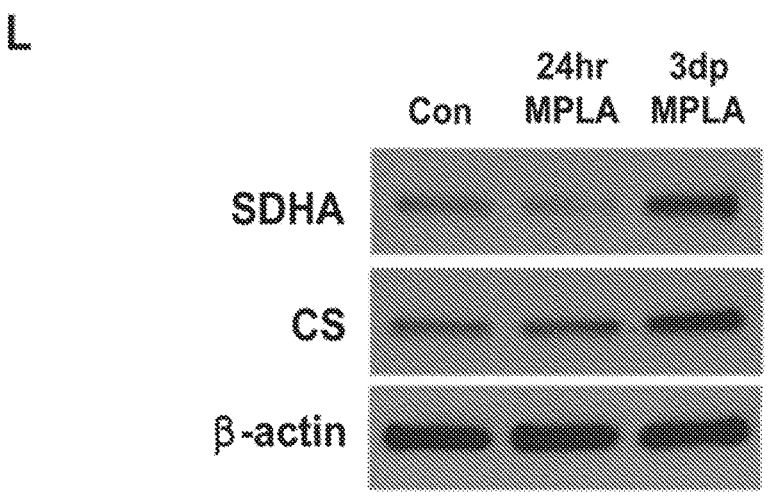
Figure 11:
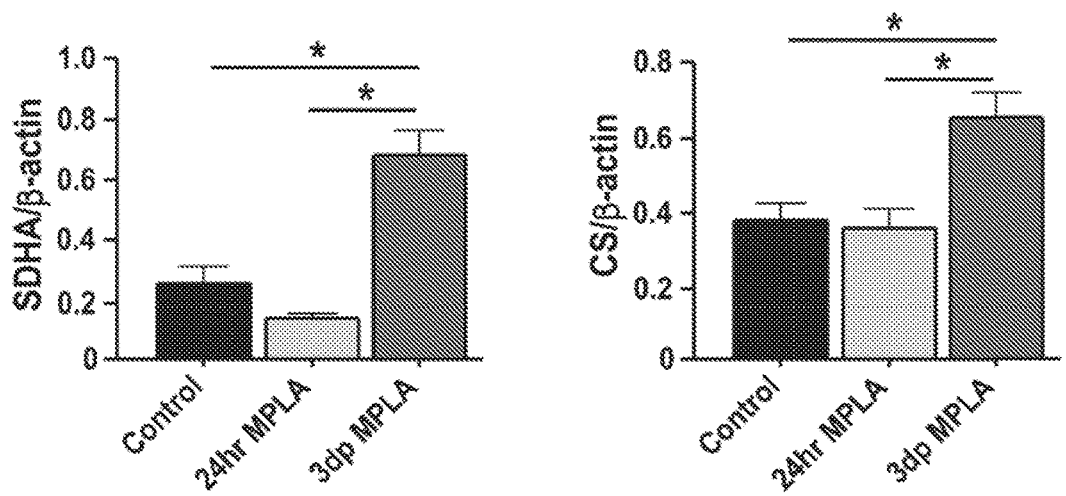

As shown in FIG. 11, MPLA drives persistent and dynamic metabolic reprogramming in macrophages. MPLA amplifies macrophage metabolism as indicated by increased glycolysis and oxygen consumption (FIG. 11, C-H), enhances ATP production (FIG. 11, I) and mitochondrial biogenesis (FIG. 11, J-L).

Unfortunately, MPLA is not available or suitable as a stand-alone immunotherapeutic. MPLA preparations are produced by hydrolysis of LPS from *Salmonella minnesota* resulting in a heterogeneous preparation. Furthermore, MPLA is currently only available as a component of a proprietary vaccine adjuvant system and not as a stand-alone immunotherapeutic.

To address these shortcomings, pure synthetic analogues of MPLA having potent biological activity were developed and examined. Phosphorylated hexaacyl disaccharides (PHADs) are MPLA analogs that have been synthesized de novo and bear potent immunotherapeutic properties. Three MPLA synthetic analogues were examined, known as phosphorylated hexaacyl disaccharide (PHAD), 3-deacyl phosphorylated hexaacyl disaccharide (3D-PHAD), and 3-D (6-acyl) phosphorylated hexaacyl disaccharide (3D(6-acyl) PHAD), that differ only in their acyl side chain conformations.

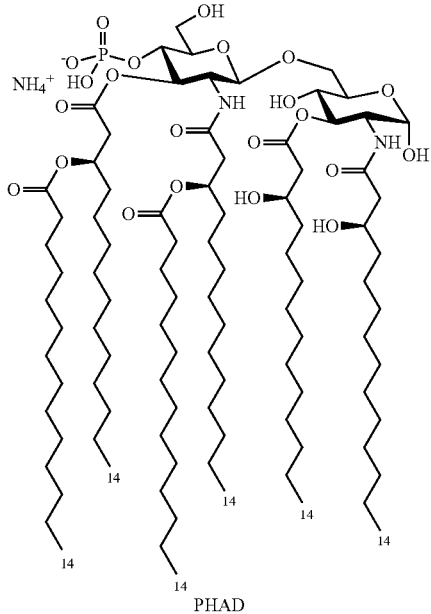

PHAD

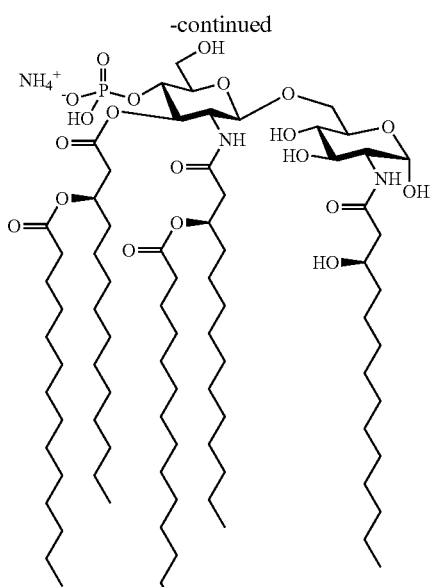

3D-PHAD

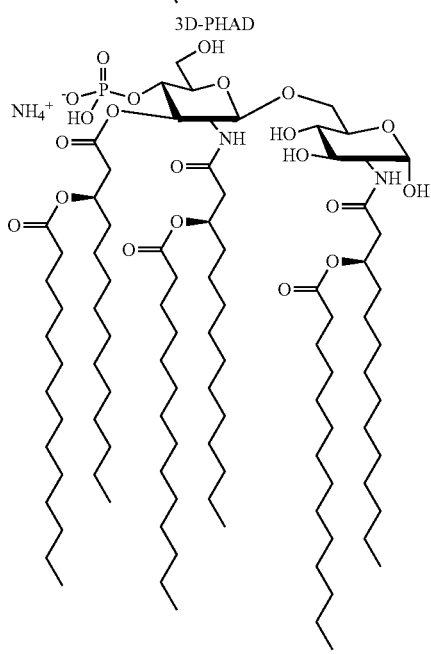

3D(6-acyl)-PHAD

In this example and specification herein, the use of the term "PHADs" can refer to the three PHAD variants (phosphorylated hexaacyl disaccharide (PHAD), 3-deacyl phosphorylated hexaacyl disaccharide (3D-PHAD), and 3-D (6-acyl) phosphorylated hexaacyl disaccharide (3D(6-acyl) PHAD)).

Figure 3:
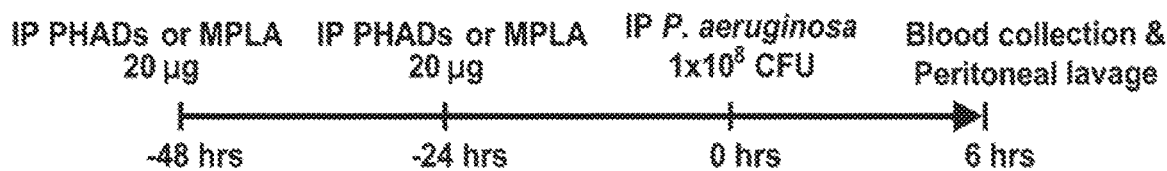
FIG. 3. PHADs protect against infection-induced hypothermia and mediate bacterial clearance post *P. aeruginosa* infection. (A) Mice received vehicle or 20 μg of MPLA or PHADs via intraperitoneal injection 48 and 24 hours prior to injecting $1\times10^8$ colony forming units of *P. aeruginosa* into the peritoneal cavity. Six hours post infection, blood was collected for plasma extraction and peritoneal lavage was performed. (B) Hourly core body temperature was measured beginning 2 hours prior to intraperitoneal infection and continued until euthanasia. Hypothermia was used as a sign of developing sepsis and physiologic dysfunction. (C) Peritoneal lavage fluid was cultured to measure bacterial burden. *$p<0.05$ compared to vehicle, and n=8-10/group, experiment was performed in triplicate.
Figure 3:
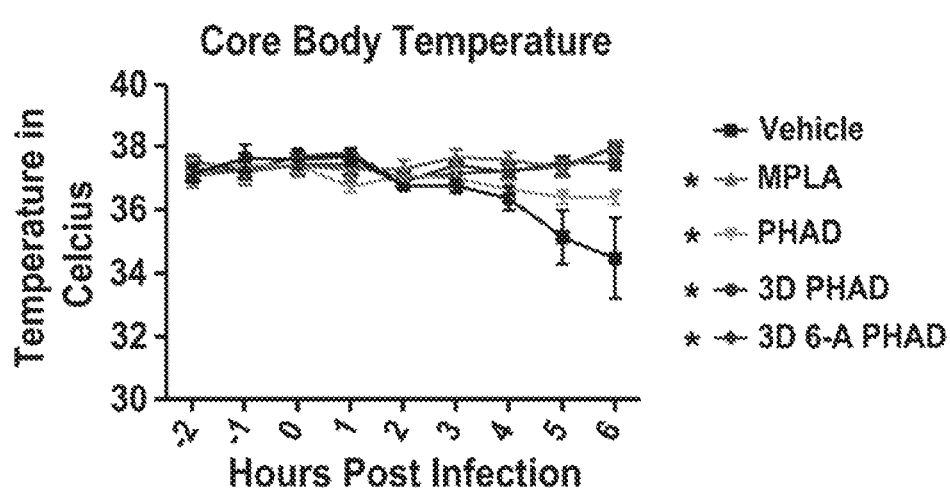
Figure 3:
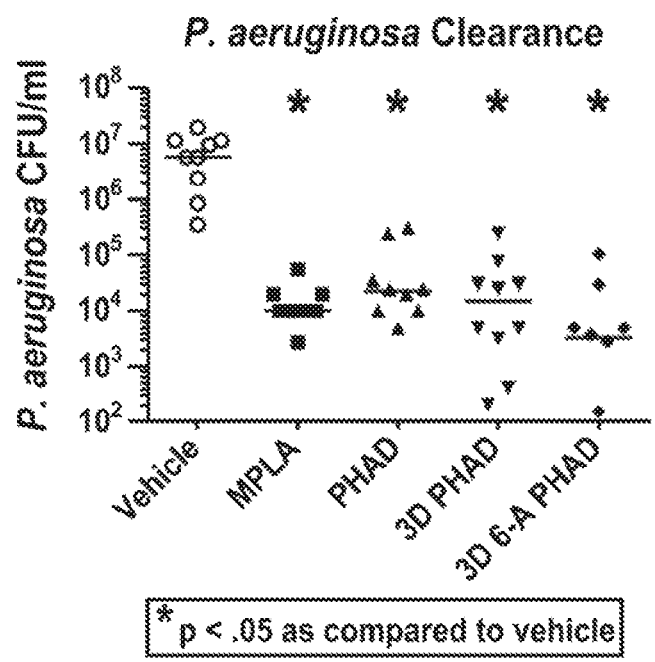

This example shows that all three compounds are useful for augmenting host resistance to *P. aeruginosa* infection (FIG. 3). Mice were treated with each of the PHADs (20 μg, IP) or MPLA on 2 consecutive days followed by intraperitoneal challenge with *P. aeruginosa* at 2 days after the second treatment. Temperature, leukocyte counts and *P. aeruginosa* colony forming units (CFU) were measured in the peritoneal cavity at 6 hours after bacterial challenge. Treatment with MPLA or any of the PHADs markedly enhanced neutrophil and monocyte recruitment to the site of infection, decreased bacterial burden and attenuated infection-induced hypothermia compared to vehicle-treated mice (FIG. 3).

Figure 8:
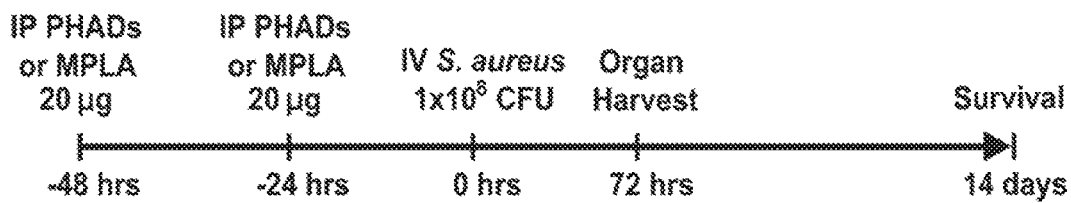
FIG. 8. PHADs induce bacterial clearance and promote survival post systemic *S. aureus* infection. (A) Mice received vehicle or 20 μg of MPLA or PHADs via intravenous injection 48 and 24 hours prior to injecting $1\times10^8$ colony forming units of *S. aureus* intravenously. (B) In one set of experiments, mice were euthanized at 72 hours post-infection and lung, spleen, and kidney tissues were harvested to measure bacterial burden. (C) In a separate set of experiments, mice underwent the same treatment with MPLA or PHADs, followed by infection with *S. aureus*. However, this group is monitored for 14 days to assess for survival. *$p<0.05$ compared to vehicle. N=13-16/group in the 3 day clearance experiments, performed in quadruplicate, and n=9-10/group, performed in triplicate.
Figure 8:
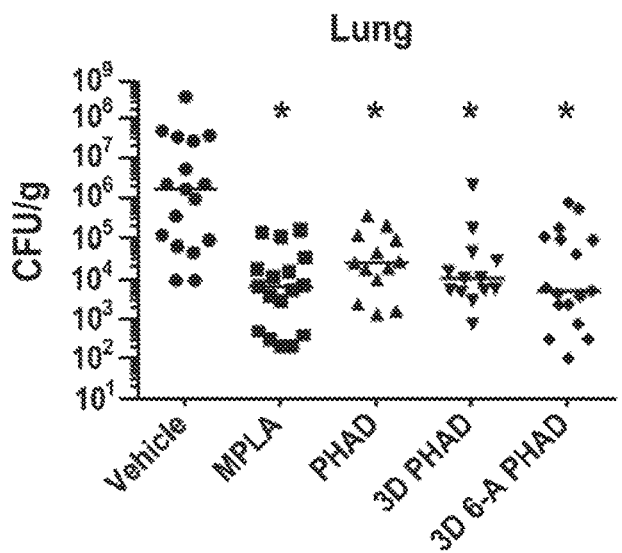
Figure 8:
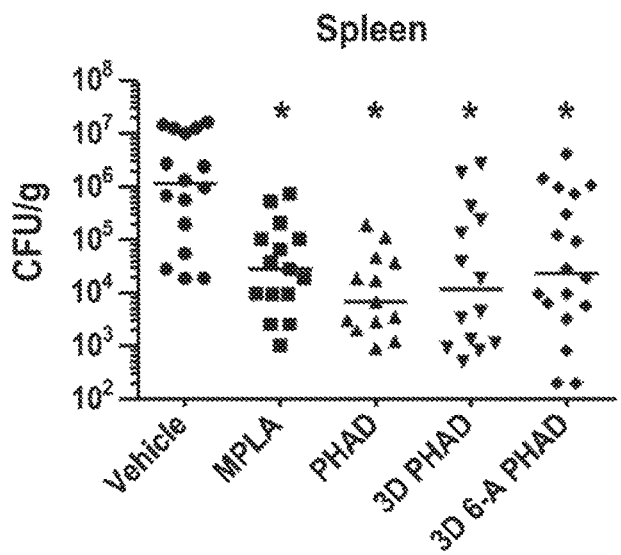
Figure 8:
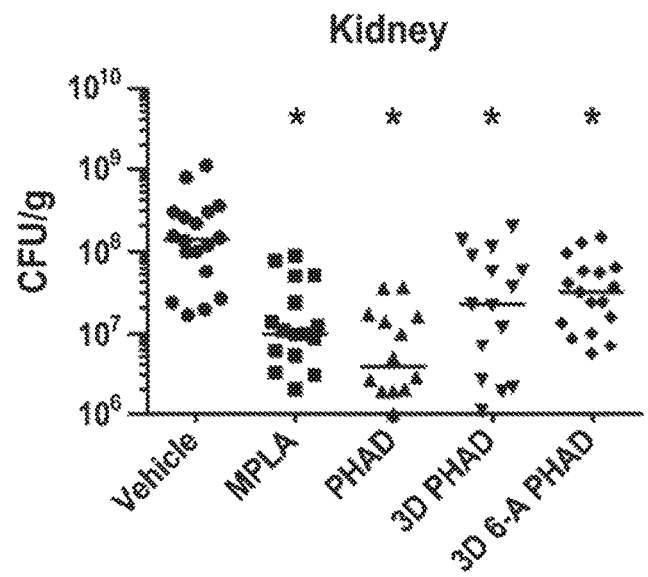
Figure 8:
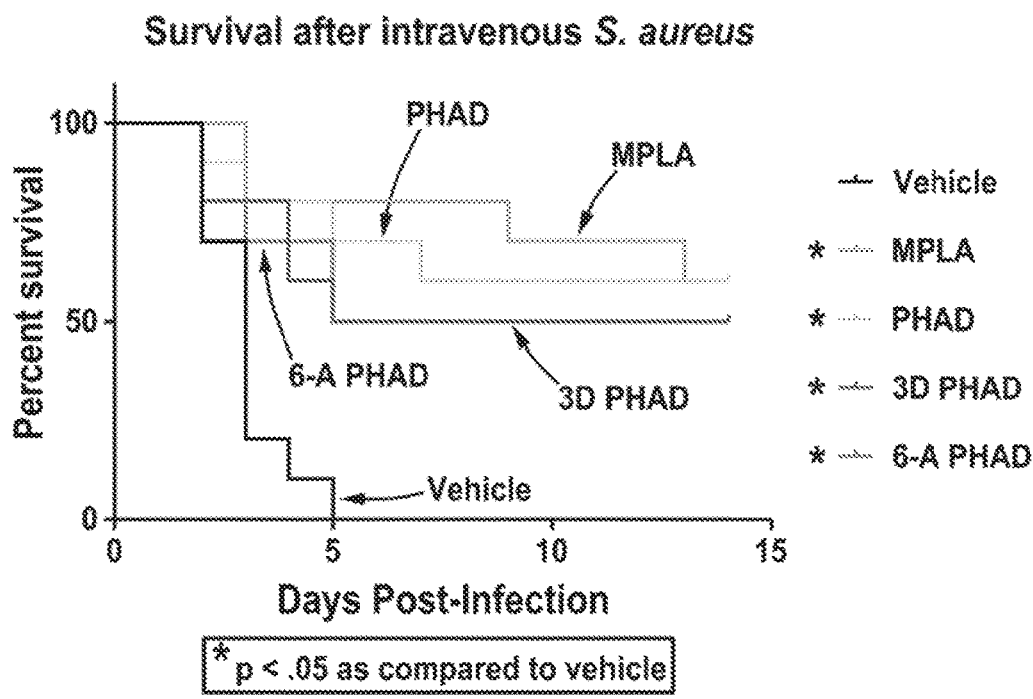

In addition, mice were analyzed for survival after intravenous *Staphylococcus aureus* infection with treatment of MPLA or PHADs. At Day 0, mice were treated with vehicle, MPLA or PHADs (20 μg/mouse). At Day 1, mice were treated with vehicle, MPLA or PHADs (20 μg/mouse). At Day 2, mice were infected with *Staphylococcus aureus* ($1 \times 10^8$ intravenously) and followed for survival. As seen in FIG. 8, mice showed improved survival after intravenous *Staphylococcus aureus* infection with treatment of MPLA or PHADs.

Figure 12:
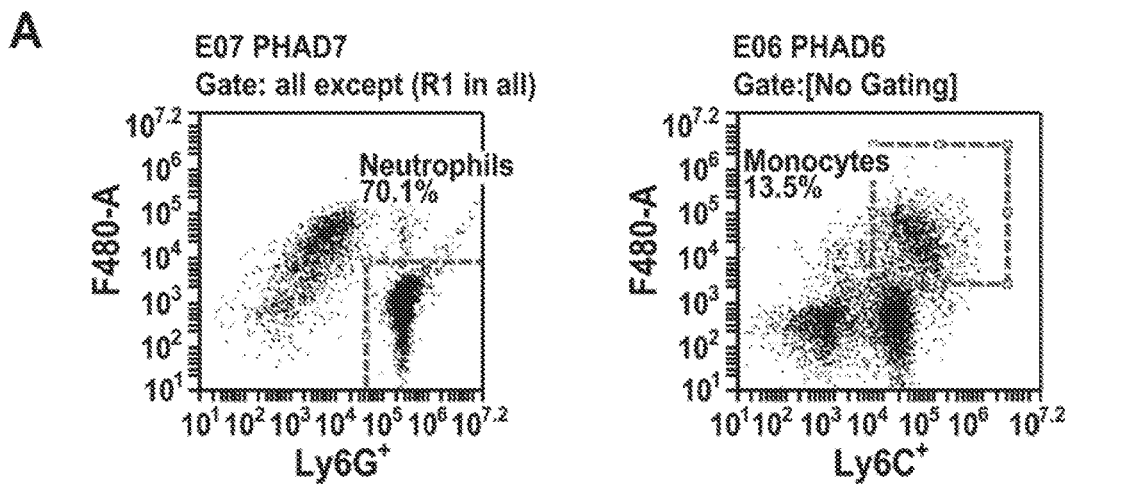
FIG. 12. PHADs induce leukocyte mobilization and recruitment post *P. aeruginosa* infection. (A) Mice received vehicle or 20 µg of MPLA or PHADs via intraperitoneal injection 48 and 24 hours prior to injecting 1×10$^8$ colony forming units of *P. aeruginosa* into the peritoneal cavity. Six hours post infection intraperitoneal leukocytes were harvested by peritoneal lavage. Cells were stained for F4/80, Ly6G, and Ly6C. Neutrophils were identified as F4/80-Ly6G$^+$. Monocytes were identified as F4/80$^+$/Ly6C$^+$. (B) Peritoneal lavage fluid percent neutrophils and monocytes. (C) Peritoneal lavage fluid total neutrophils and monocytes. *p<0.05 compared to vehicle, +p<0.05 compared to PHAD, and n=8-10/group, performed in triplicate.
Figure 12:
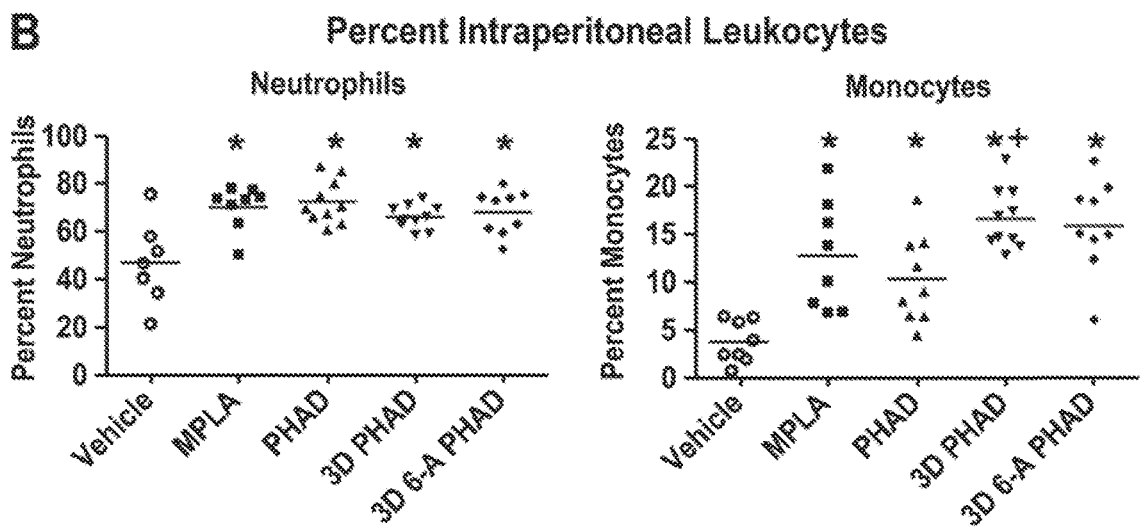
Figure 12:
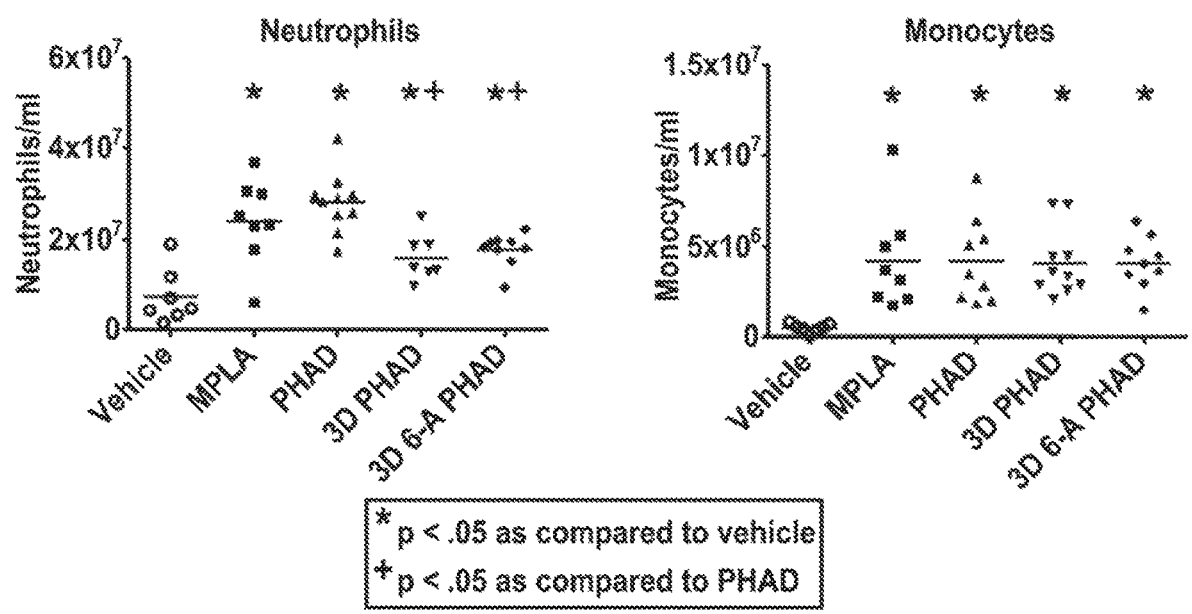
Figure 13A:
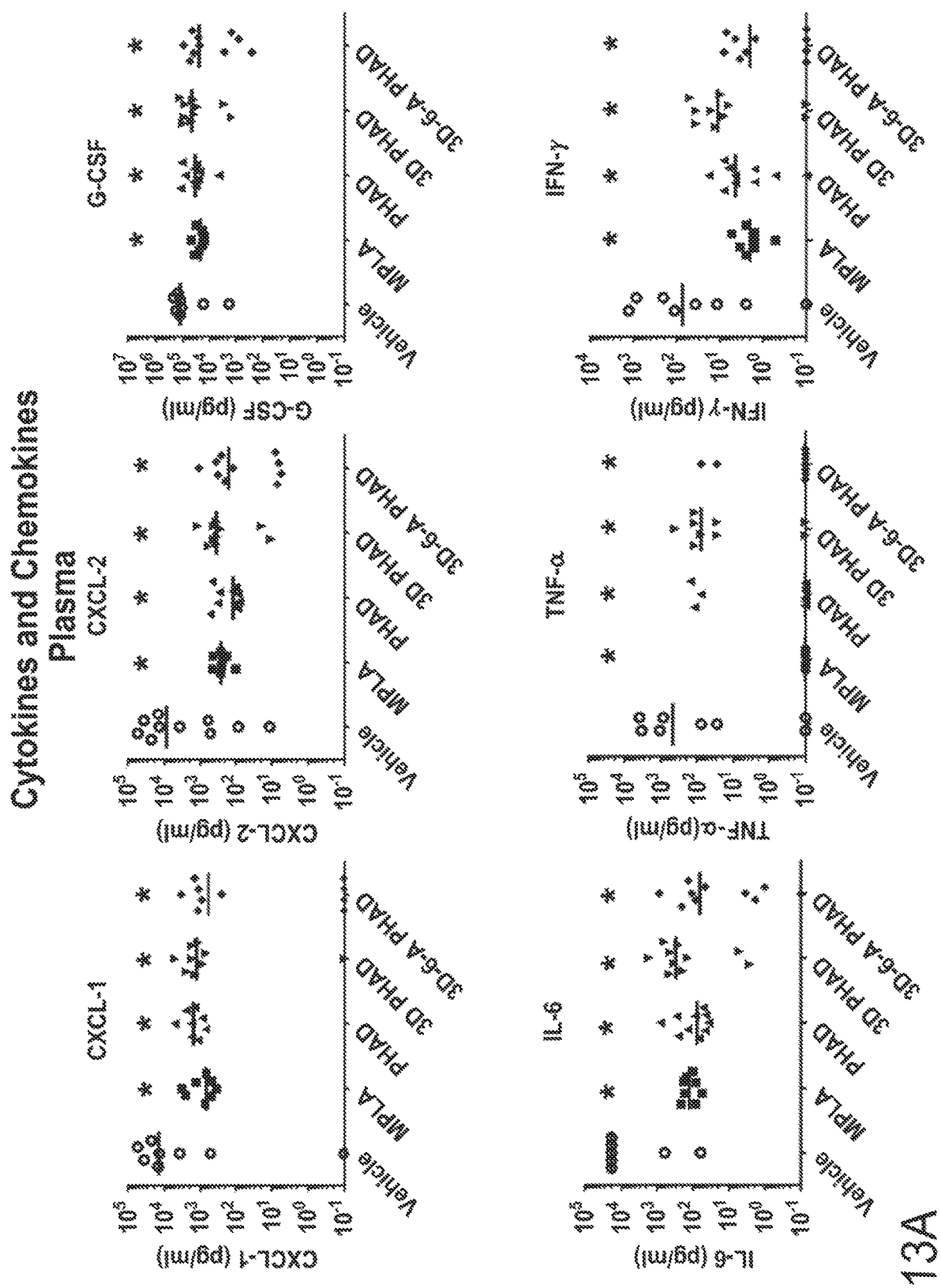
FIG. 13A-13B. PHADs attenuate plasma and peritoneal cytokines and chemokine production post *P. aeruginosa* infection. (A) Mice received vehicle or 20 µg of MPLA or PHADs via intraperitoneal injection 48 and 24 hours prior to injecting 1×10$^8$ colony forming units of *P. aeruginosa* into the peritoneal cavity. Six hours post infection blood was collected and peritoneal lavage performed. Blood was processed for plasma extraction which was analyzed for cytokine and chemokine concentrations. (B) Peritoneal lavage fluid was analyzed for cytokine and chemokine concentrations. *p<0.05 compared to vehicle, and n=8-10/group, performed in triplicate.
Figure 13B:
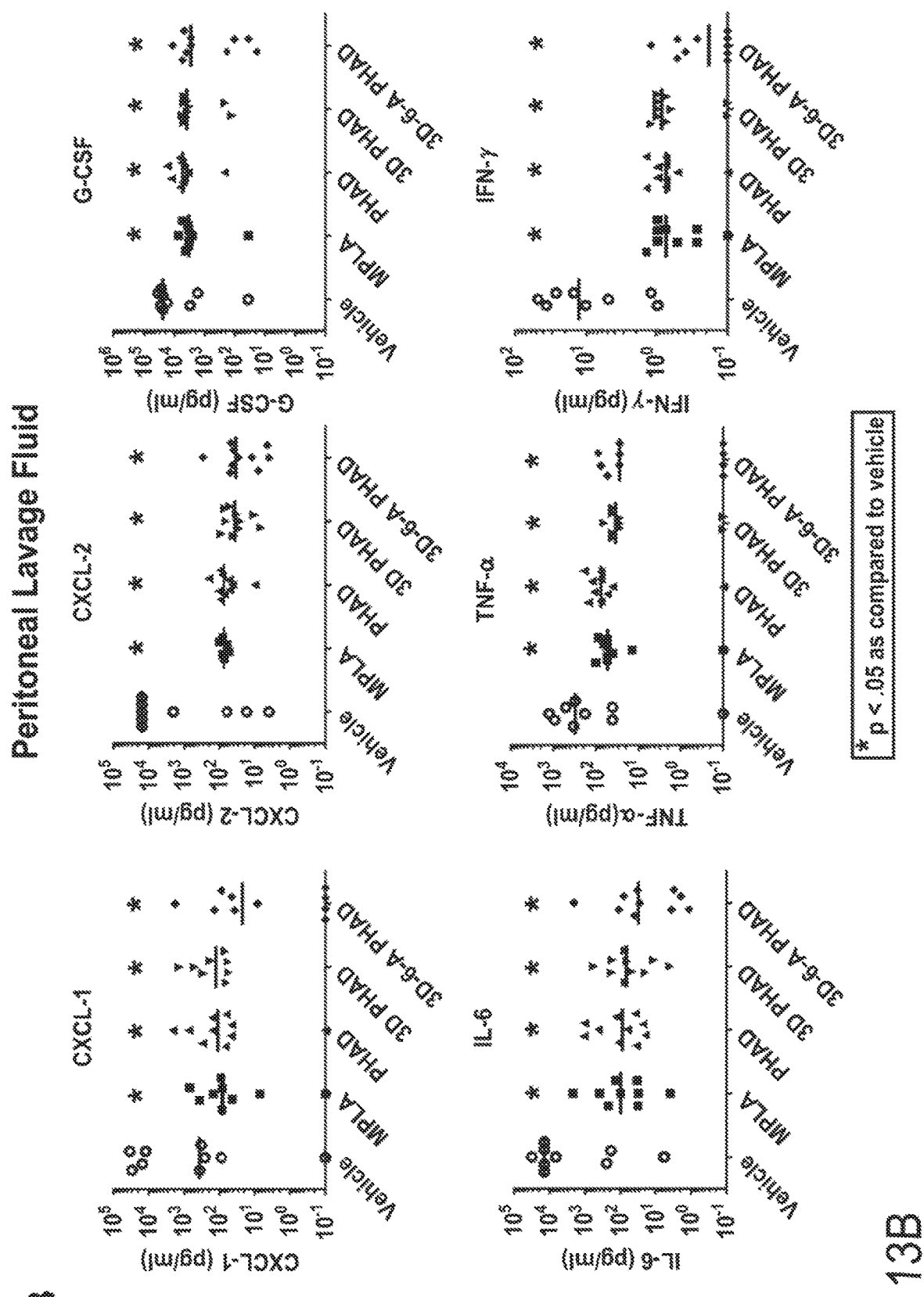

Further, as seen in FIG. 12, PHADs induce leukocyte mobilization and recruitment post *P. aeruginosa* infection. In addition, PHADs attenuate plasma and peritoneal cytokines and chemokine production post *P. aeruginosa* infection (FIG. 13).

PHADs are unique and allow a new class of clinically useful immunotherapeutics. Second, the use of TLR4-based immunotherapy to augment antimicrobial immunity and enhance the efficacy of antibiotics is a novel approach. Innovative solutions are needed to expand the armamentarium available to prevent and treat infection with antibiotic resistant pathogens and other emerging infectious diseases.

PHADs can be used in models of burn and infection. These PHAD-based immunotherapies also have broad application in critically ill and other vulnerable populations.

Determining Formulation, Dose and Duration for PHADs

High throughput in vivo models for testing the efficacy of TLR4 agonists in mice have been developed. Dose and formulation of PHADs are tested in models of *P. aeruginosa* burn wound infection and systemic *S. aureus* and *C. albicans* infection to validate the findings our high throughput studies. The mouse model is important for the identification of PHAD dosing and formulation because it allows for rapid and cost effective testing prior to moving to the sheep model for validation of the identified formulation and dose.

These experiments also determine the IV formulation and dose of 3D-PHAD. Two formulation strategies are tested. One formulation employs an organic solvent (0.2% triethylamine) to facilitate aqueous solution of 3D-PHAD. The second employs liposomal encapsulation formulation. Previously, a 0.2% triethylamine formulation was used at a dose of 20 μg/mouse to perform head to head comparison of PHADs and MPLA. Both agents are efficacious at that dose (FIG. 3). The 0.2% triethylamine and liposomal formulations are examined at doses of 200, 20, 2 and 0.2 μg/mouse.

High Throughput In Vivo Infection Model.

Mice receive IV treatment with vehicle or PHADs on days 2 and 3 after burn injury and are challenged with *P. aeruginosa* ($1 \times 10^8$) by intraperitoneal injection on day 4. At 6 hours after microbial challenge, rectal temperature is measured and peritoneal lavage performed using 2 ml of phosphate buffered saline. Neutrophil ($Ly6G^+$, $F4-80^-$) and monocyte ($Ly6G^-$, $Ly6C^+$) numbers in peritoneal lavage fluid are determined using flow cytometry and bacterial burden is determined by serial dilution and culture of peritoneal lavage fluid. It is recognized that intraperitoneal infection with *Pseudomonas aeruginosa* is not common in the clinical setting of burn injury. However, the peritoneal cavity provides a defined and easily accessible site to measure leukocyte accumulation and bacterial burden during infection in vivo. Therefore, the intraperitoneal challenge model is used to determine the formulation and dose of PHADs as well as duration of action. The model has worked well in previous studies (18, 20, 21). The measured endpoints have proven to be predictive of the efficacy of TLR4 agonists in clinically relevant models of infection.

Test Groups

In all experiments, the efficacy and biology of PHADs are compared to vehicle. In triethylamine formulation experiments, PHADs are solubilized in sterile water containing 0.2% triethylamine followed by sonication and dilution in lactated Ringer's (LR) solution for administration. The same formulation less PHADs serve as vehicle control. Liposomes containing LR serve as vehicle control. The experiments are replicated in triplicate (n=10 mice/group) and results are combined for a total N=30/group. Male and female mice are used in equal numbers in all experiments. Two formulations (aqueous and liposomal) are tested at 4 doses along with associated controls for a total of 480 mice. Test drugs (PHADs and vehicle) are prepared and provided in a blinded fashion. Investigators are blinded to test groups until all experiments are completed.

Determination of Duration of Action.

Figure 4:
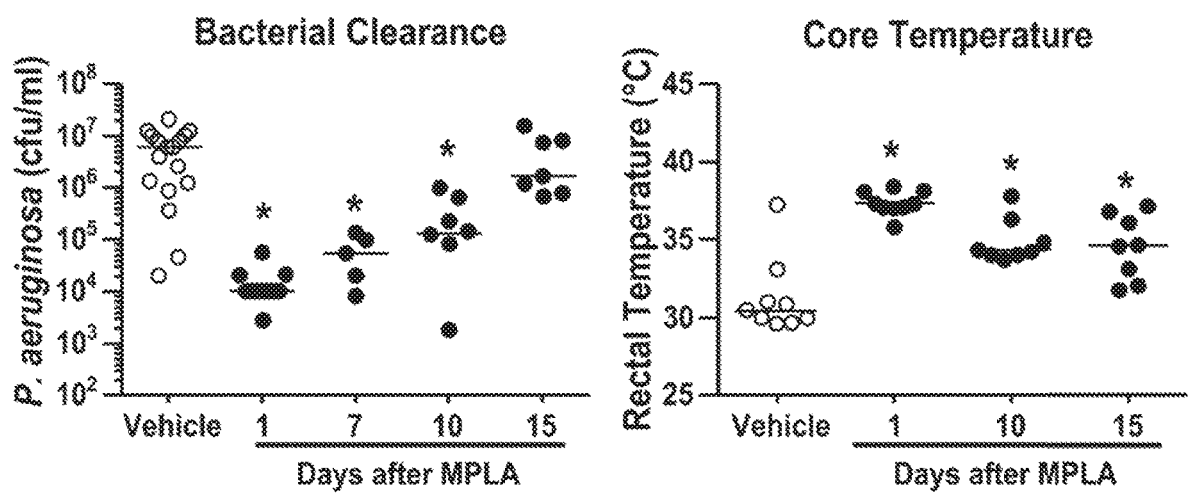
FIG. 4. Duration of MPLA activity. Mice were treated with MPLA (20 μg IP) for 2 consecutive days and challenged with *P. aeruginosa* at the designated times after the last MPLA treatment. *$<0.05$ compared to vehicle control.

It is important to know how long the effect of PHADs lasts to guide dosing frequency. Studies were performed with MPLA that show a duration of action of up to 10 days. Mice were treated with MPLA on 2 consecutive days (20 μg, IP) followed by intraperitoneal challenge with *Pseudomonas aeruginosa* ($1 \times 10^8$) at 1, 7, 10 or 15 days after the last MPLA treatment (FIG. 4). MPLA-treated mice had significantly lower bacterial burden at 1, 7 and 10 days after treatment compared to vehicle-treated mice. Bacterial clearance returned to control levels by day 15. However, attenuation of hypothermia persisted until day 15 (FIG. 4).

Testing of PHADs in Clinically Relevant Models of Infection.

Both the aqueous and liposomal formulations of PHADs are tested in clinically relevant models of *Pseudomonas* burn wound infection and systemic infection with *S. aureus* or *C. albicans*.

Effect of PHADs Treatment on Physiologic Function, Organ Injury, Bacterial Clearance and Survival During *Pseudomonas* Burn Wound Infection.

An established burn wound model is employed (29-31). Briefly, under isoflurane anesthesia, the dorsum of mice is shaved and 1 mL of 0.9% normal saline is injected along the dorsum to protect underlying tissues from thermal injury. Mice are placed in a supine position within a plastic template containing an oval-shaped opening corresponding to ~20% of the total body surface area (TBSA). The exposed dorsal skin is immersed into a water bath at 98° C. for 10 seconds. Fluid resuscitation with 2 ml of Lactated Ringer's solution is achieved via intraperitoneal injection immediately following the burn injury. IV treatment with PHADs is initiated on days 2 and 3 post-burn. Vehicle-treated mice serve as controls. The burn wound is inoculated with $1 \times 10^8$ of *P. aeruginosa* on day 4. Rectal temperature is measured twice daily beginning 1 day after infection as an indicator of sepsis progression. On day 3 after infection, arterial blood is obtained for blood gas analysis (pH, $pCO_2$, $HCO_3$ and base deficit) and measurement of liver enzymes (AST/ALT) and BUN/creatinine to provide information on acid-base derangements, lung injury, liver injury and kidney injury, respectively. Blood, burn wound eschar and lung is harvested at the same time points for culture to assess bacterial burden. A separate cohort of mice are monitored for 14 days after infection to assess survival.

Effect of PHAD Treatment on Physiologic Function, Organ Injury, Microbial Burden and Survival During Systemic *S. aureus* or *C. albicans* Infections.

The established burn wound model is induced as described above. IV treatment with PHADs is initiated on days 2 and 3 post-burn. Vehicle-treated mice serve as controls. Mice receive intravenous challenge with $1 \times 10^8$ *S. aureus* or *C. albicans* on day 4. Rectal temperature is measured twice daily beginning 1 day after infection as an indicator of sepsis progression. On day 3 after infection, arterial blood is obtained for blood gas analysis and measurement of liver enzymes (AST/ALT) and BUN/creatinine to assess acid-base derangements, lung injury, liver injury and kidney injury, respectively. Blood and tissues (lung, spleen and kidney) is harvested at the same time points for culture to assess bacterial burden in all experimental groups. A separate cohort of mice is monitored for 14 days after infectious challenge to assess survival.

For studies focused on determining physiologic dysfunction, organ injury and bacterial clearance, experiments are replicated in triplicate (n=10 mice/group) and results are combined for a total N=30/group. For survival studies, experiments are replicated three time (n=10 mice/group) and results are combined for a total N=30/group. Male and female mice are used in equal numbers in all experiments. Two formulations and controls are tested against 3 clinically relevant models of infection. Test drugs (PHADs and vehicle) are prepared and provided in a blinded fashion. Investigators are blinded to test groups until all experiments are completed.

Assessment of Safety and Efficacy of PHADs in Ovine (Sheep) Models.

Data from the rodent *P. aeruginosa* infection model shows that the host response to infection is substantially improved by PHAD treatment. The sheep model is used to determine formulation and dose of PHADs and its safety and efficacy in clinically relevant models of burn and infection. The sheep model is attractive because sheep respond to LPS and MPLA in a manner very similar to humans (32, 33).

Figure 5:
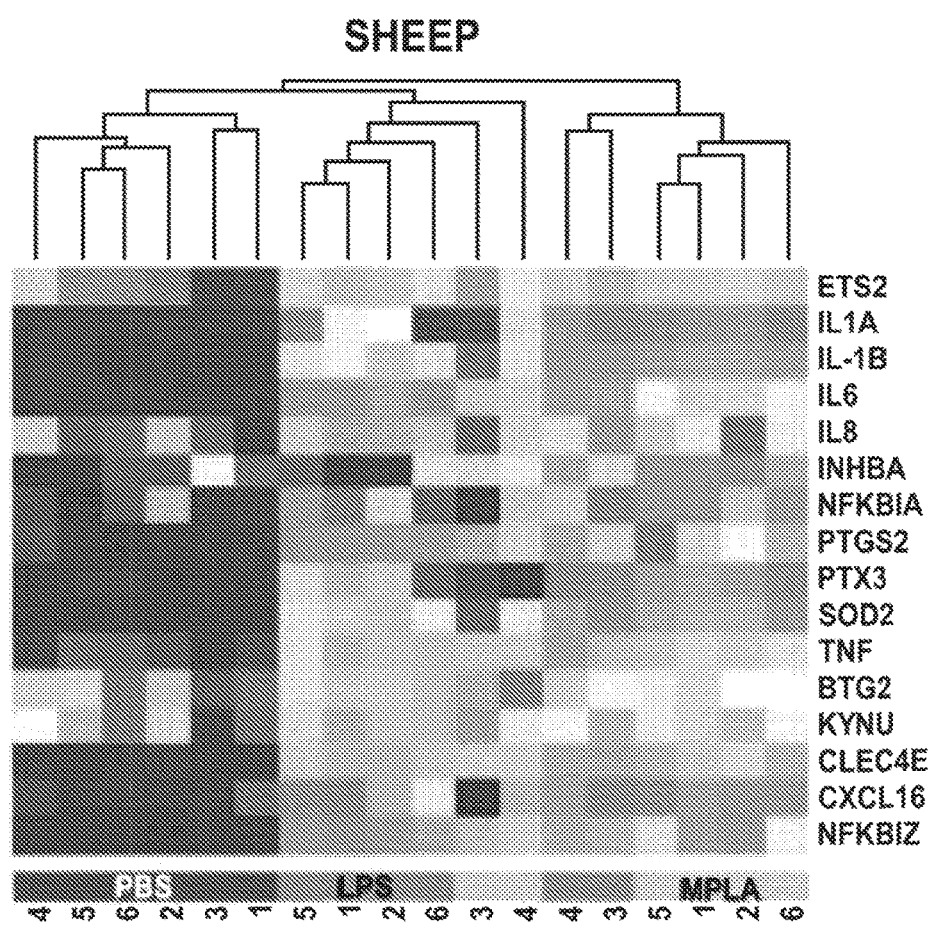
FIG. 5. Hierarchical cluster of the 16 sheep-human orthologues similarly expressed in both species after MPLA treatment (>1.5-fold, paired t-test p values<0.05).
Figure 5:
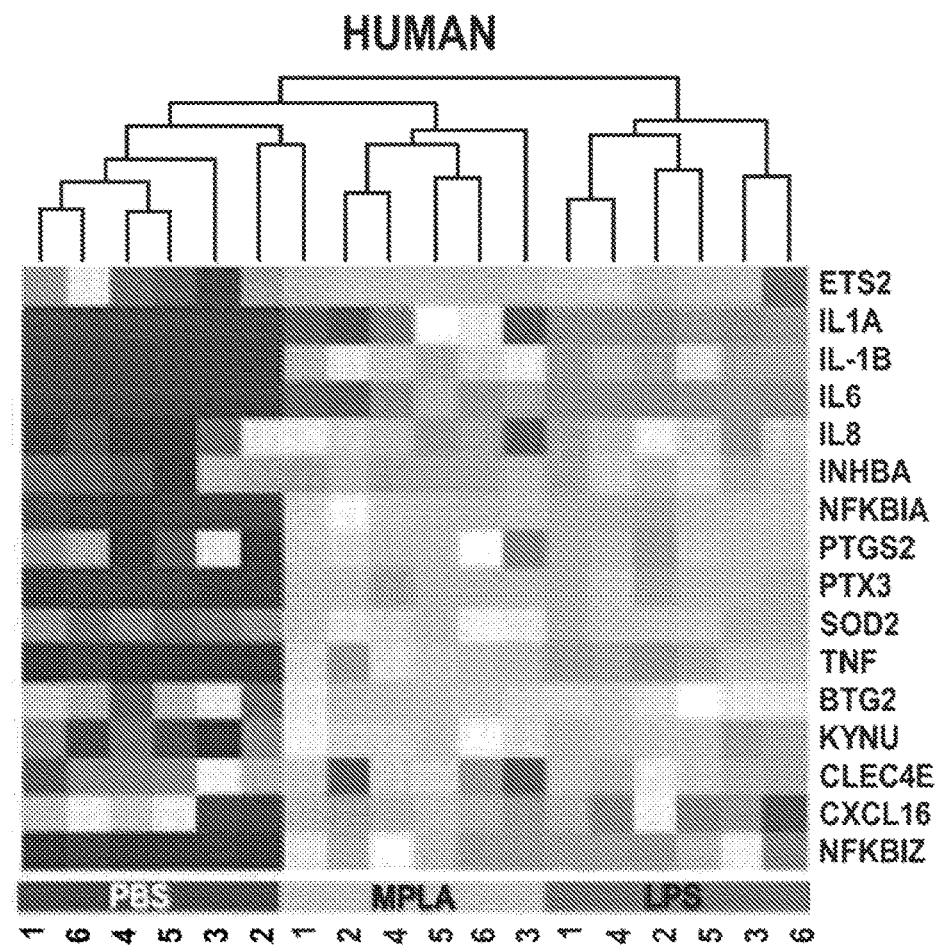

Pre-clinical drug development requires appropriate models. Using rodent models, data was provided showing that MPLA augments host resistance to infection with *Pseudomonas aeruginosa, Staphylococcus aureus* and *Candida albicans*. Further studies show that PHADs (including 3D-PHAD) are as efficacious as MPLA in a high throughput rodent model of *Pseudomonas aeruginosa* infection. However, the ovine model provides many advantages for the pre-clinical development of PHADs. To assess the ovine model for studying TLR4 ligands, the genomic responses of sheep and human blood after stimulation with MPLA and LPS were compared (FIG. 5). Venous blood from six healthy human adult volunteers (~28 years old) and six healthy adult sheep (~3 years old), was mixed with 30 µL of PBS, LPS (1 µg/mL) or MPLA (10 µg/mL) and incubated at room temperature for 90 minutes. Gene expression analysis was performed using an Agilent Bioanalyzer with the RNA6000 Nano Lab Chip. These published results show that 11,431 human and 4,992 sheep probes were detected above background (37). Among them 1,029 human and 175 sheep genes were differentially expressed at a stringency of 1.5-fold change (p<0.05). Of the 175 sheep genes, 54 had a known human orthologue. Among those genes, 22 had >1.5-fold changes in human samples. Genes of inflammatory mediators, such as IL-1, IL-6 and IL-8, TNF alpha, NF-kappaB, ETS2, PTGS2, PTX3, CXCL16, KYNU, and CLEC4E were similarly (>2-fold) upregulated by LPS and MPLA in both species (FIG. 5). Thus, the genomic responses of peripheral blood to LPS and MPLA in sheep and humans are quite similar.

Figure 6:
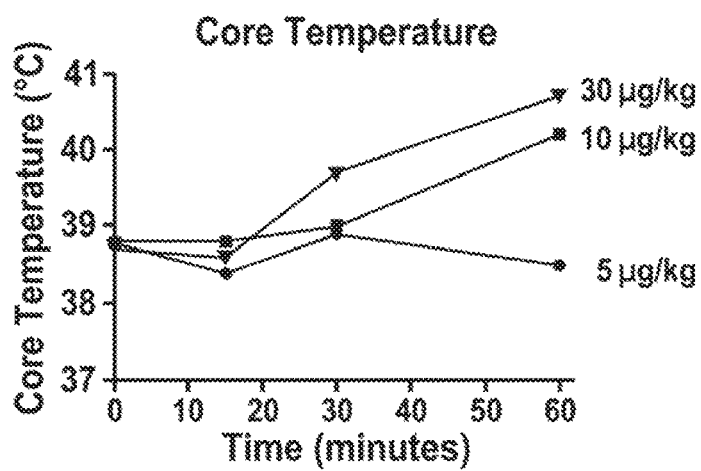
FIG. 6. Effects of MPLA infusion at the indicated doses over 10 minutes. Endpoints were recorded over a 1 hour period beginning at the end of the MPLA infusion.
Figure 6:
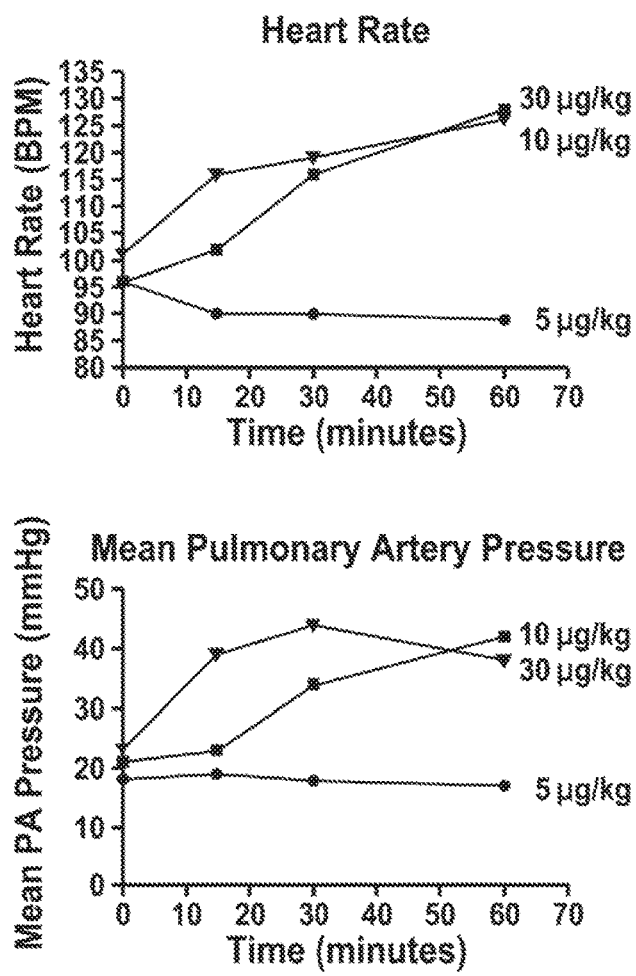

In further studies, the response of sheep to MPLA infusion was assessed (FIG. 6). Instrumented sheep received infusions of MPLA at doses of 5, 10 or 30 ug/kg in 10 ml of endotoxin-free lactated Ringer's solution over 10 minutes. Physiological parameters were monitored for 1 hour after MPLA infusion. Infusion of MPLA at 5 ug/kg did not change temperature, heart rate or mean pulmonary artery pressure but all parameters were increased after infusion 10 or 30 ug/kg of MPLA (FIG. 6). Results from this study are remarkably similar to findings reported in humans by Astiz et al (24) who showed that humans receiving MPLA infusions show subjective changes consistent with systemic inflammation at an MPLA dose of 10 ug/kg, but not at lower doses. These observations indicate that sheep have sensitivity to MPLA that is very similar to humans.

Figure 7:
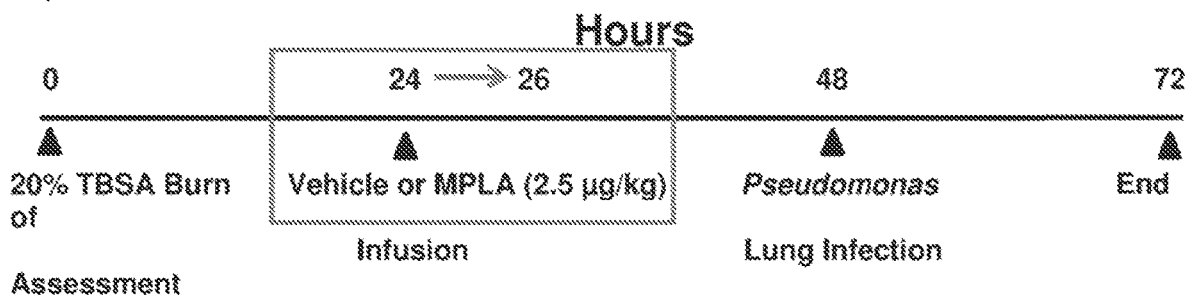
FIG. 7. MPLA infusion causes transient physiologic changes in burned sheep. Sheep received 20% total body surface area burn followed 24 hours later by vehicle or MPLA (2.5 micrograms/kg) infusion. Core body temperature, hemodynamics and pulmonary mechanics were measured for 2 hours after initiation of MPLA or vehicle infusions. MPLA infusion increased core body temperature beginning at 45 minutes after the initiation of infusion that peaked at 75 minutes and remained elevated at 2 hours after treatment. A transient increase in heart rate (HR) and decrease in mean arterial blood pressure (MAP) were also observed in MPLA-treated sheep. Heart rate as significantly increased at 30-75 minutes after MPLA infusion and returned to baseline at 90 minutes. Mean arterial pressure was significantly decreased at 45 and 60 minutes after MPLA infusion. Cardiac index (CI), central venous pressure (CVP) and systemic vascular resistance (SVRI) were minimally impacted by MPLA infusion.
Figure 7:
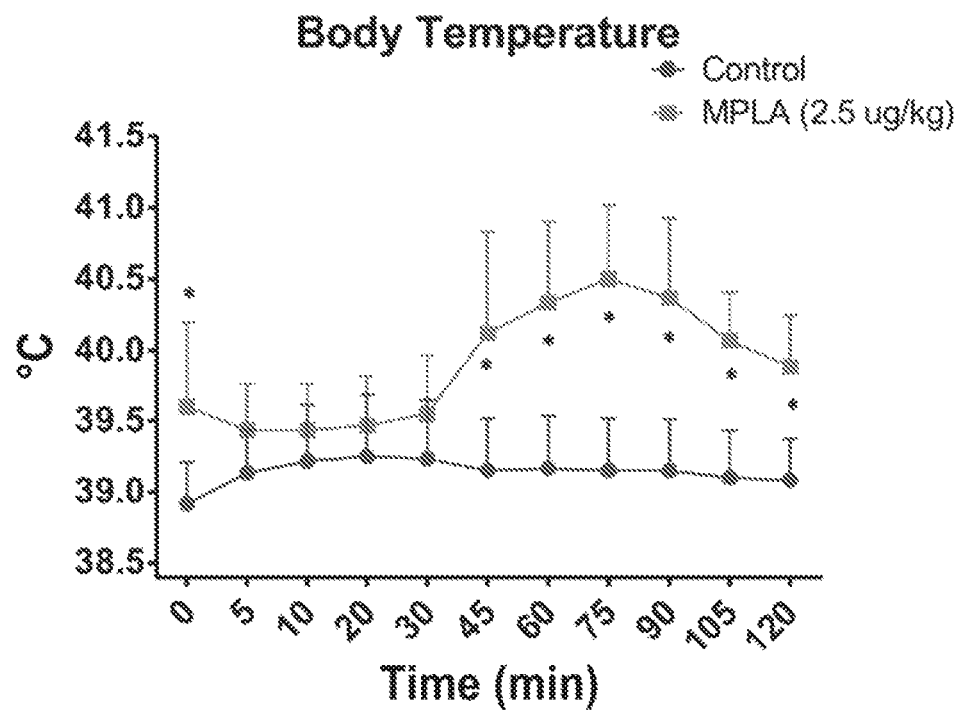
Figure 7:
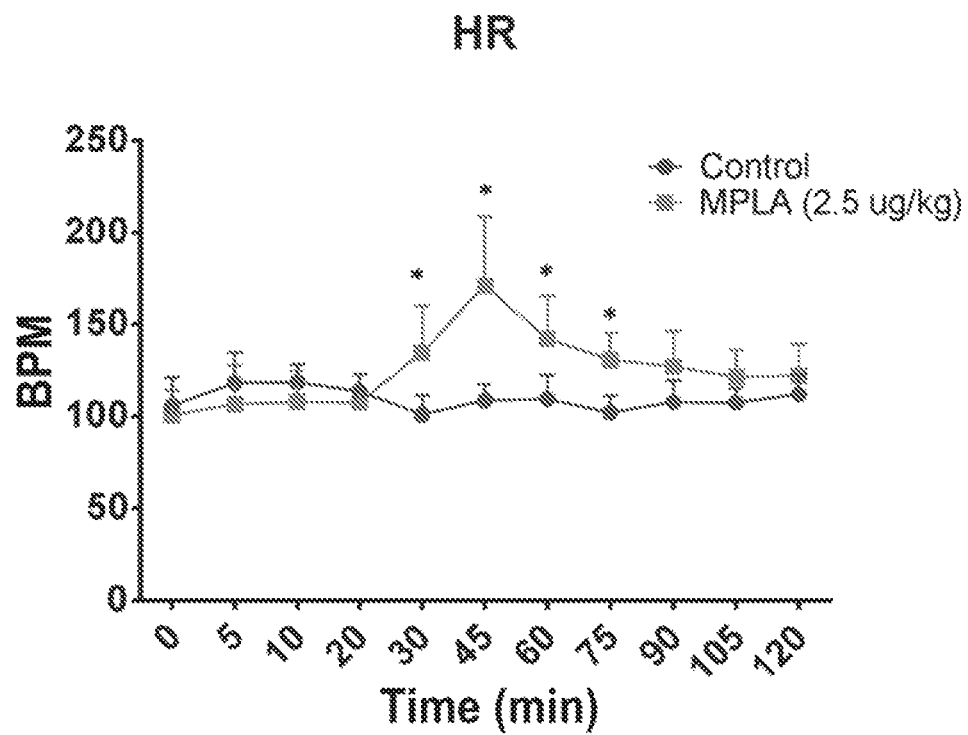
Figure 7:
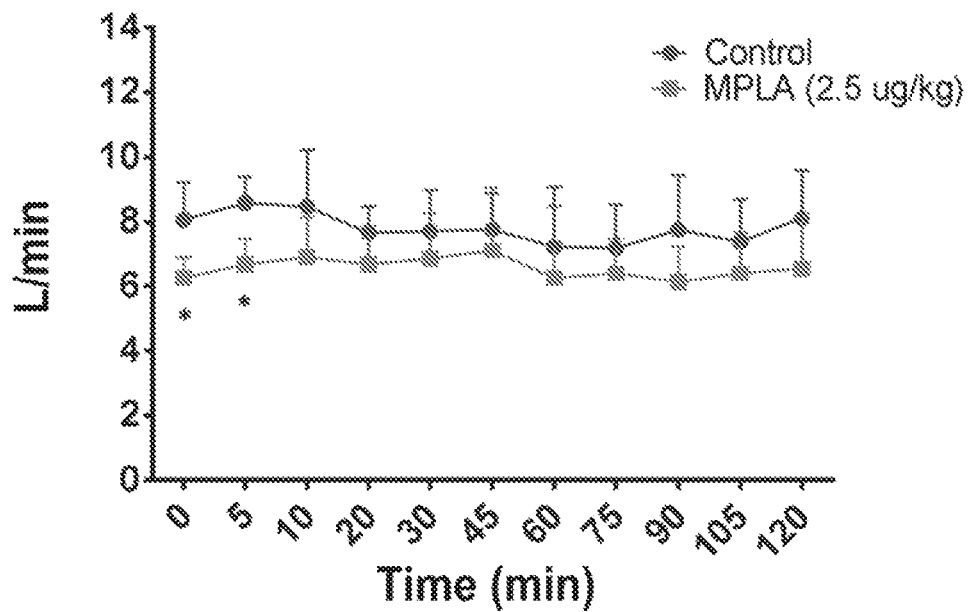
Figure 7:
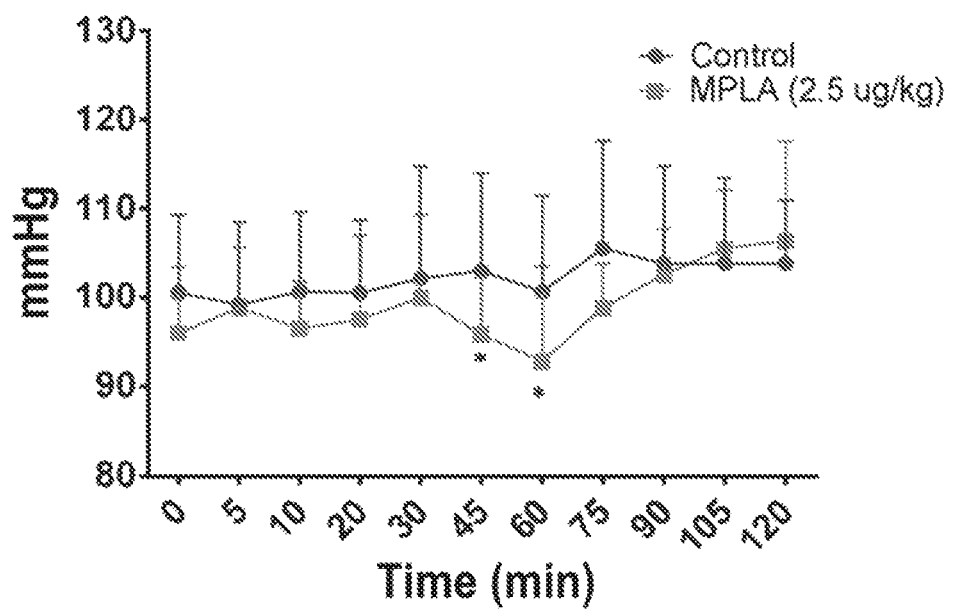
Figure 7:
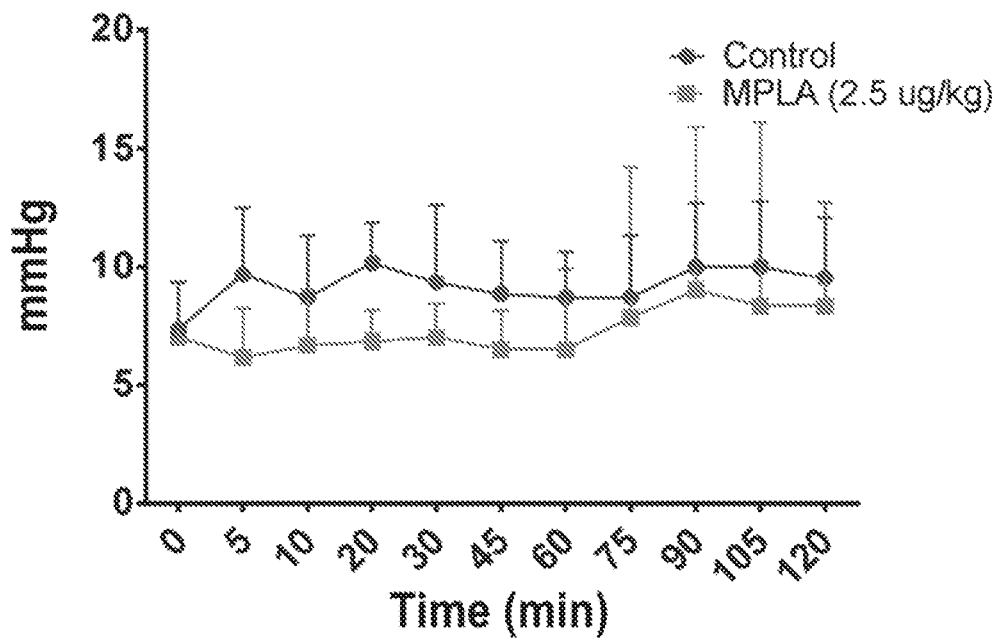
Figure 7:
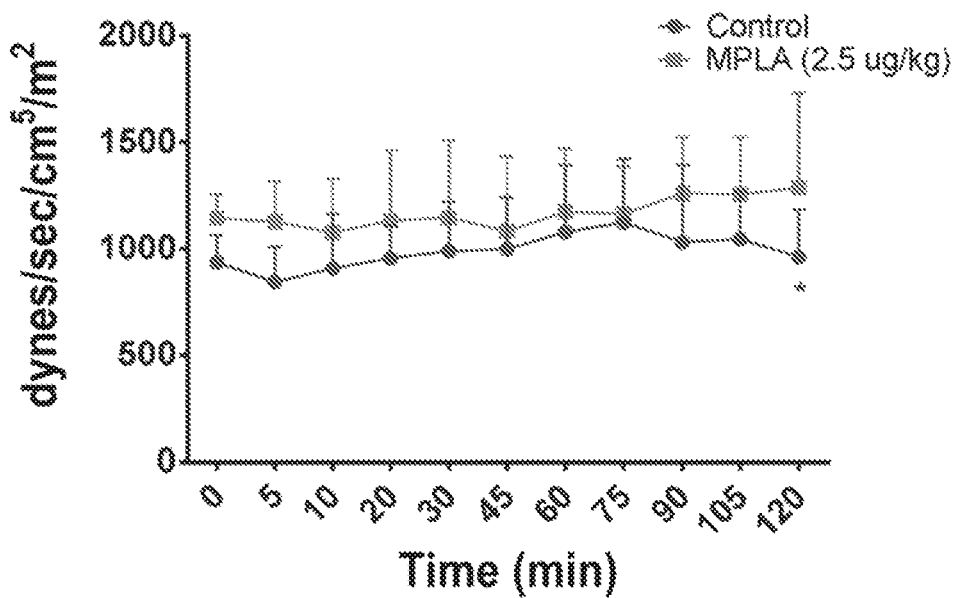
Figure 14:
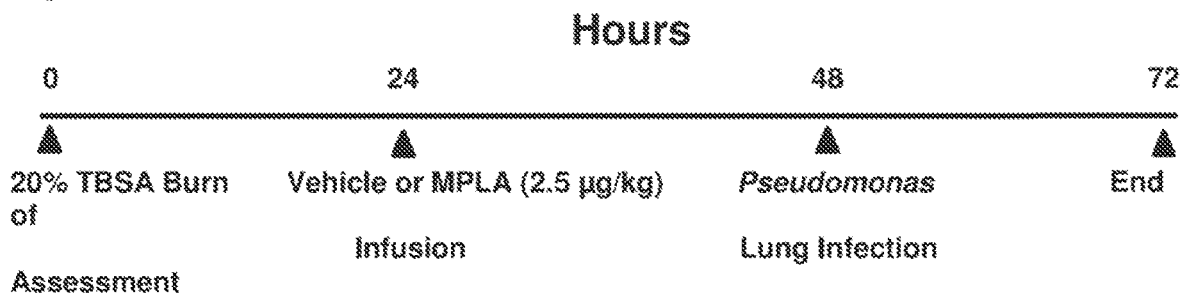
FIG. 14. MPLA treatment improves oxygenation and pulmonary mechanics and attenuates lactate production in sheep with *Pseudomonas* pneumonia. Studies were undertaken to assess oxygenation, pulmonary mechanics and hemodynamics in burned sheep treated with vehicle or MPLA prior to intrapulmonary challenge with *P. aeruginosa*. Sheep received a 20% total body surface area thermal burn followed 24 hours later by MPLA infusion. Intrapulmonary *P. aeruginosa* infection was induced at 24 hours after MPLA infusion. All sheep survived the 72 hour study period. Hemodynamics and pulmonary function were measured for 24 hours after *Pseudomonas* infection. PaO$_2$/FiO$_2$ ratio significantly declined in sheep within 3 hours after *Pseudomonas* infection in vehicle- and MPLA-treated sheep. Oxygenation was significantly better in MPLA-treated sheep compared to controls as indicated by significantly higher PaO$_2$/FiO$_2$ ratio, improved oxygenation index and decreased shunt fraction. PaCO$_2$ was not significantly different between groups. The decrease in plasma protein caused by pulmonary infection trended towards attenuation in MPLA-treated sheep, although the difference was not significantly different between groups. Infection caused an increase in plasma lactate concentration, which was significantly lower in MPLA-treated sheep compared to controls.
Figure 14:
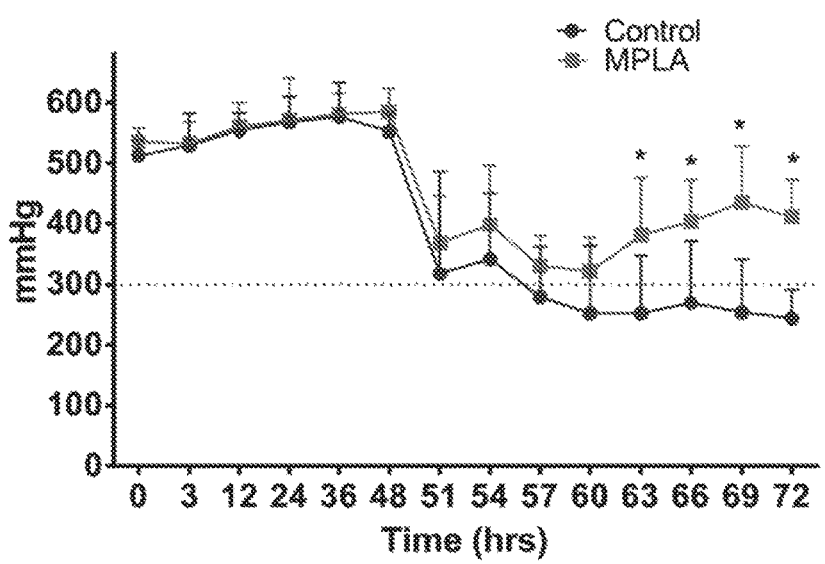
Figure 14:
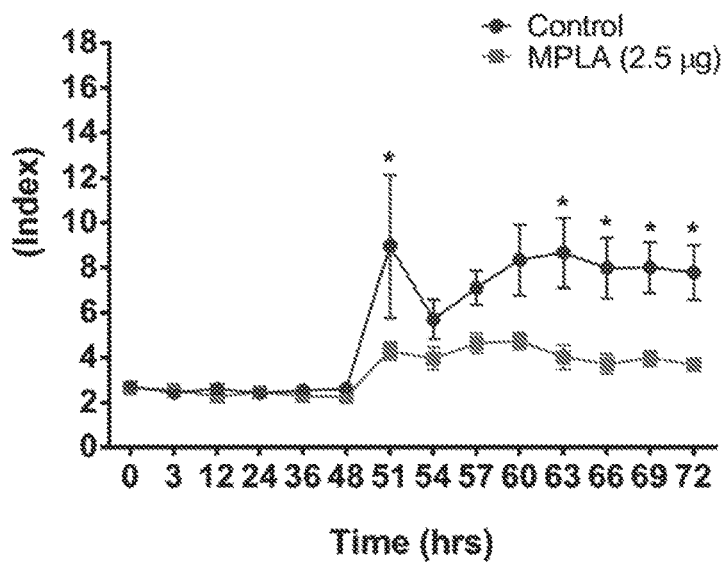
Figure 14:
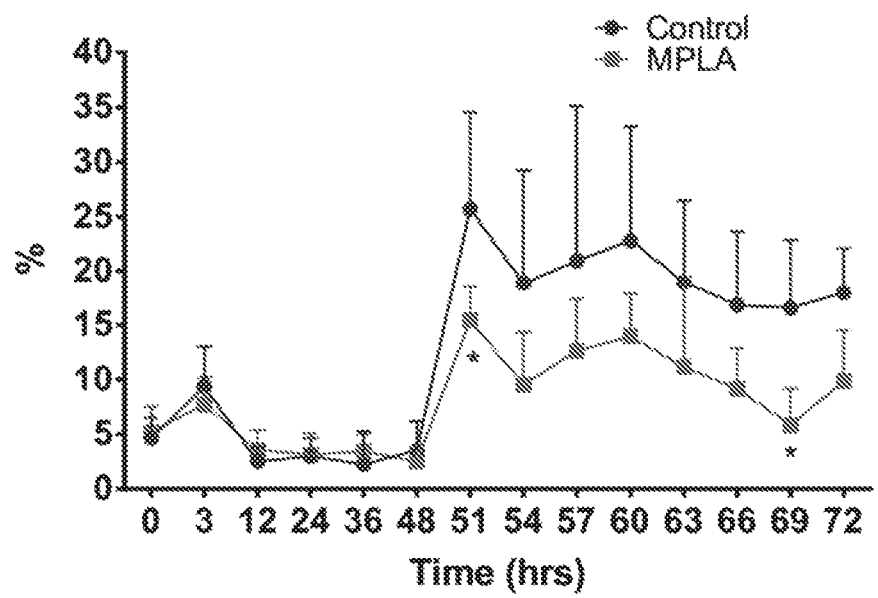
Figure 14:
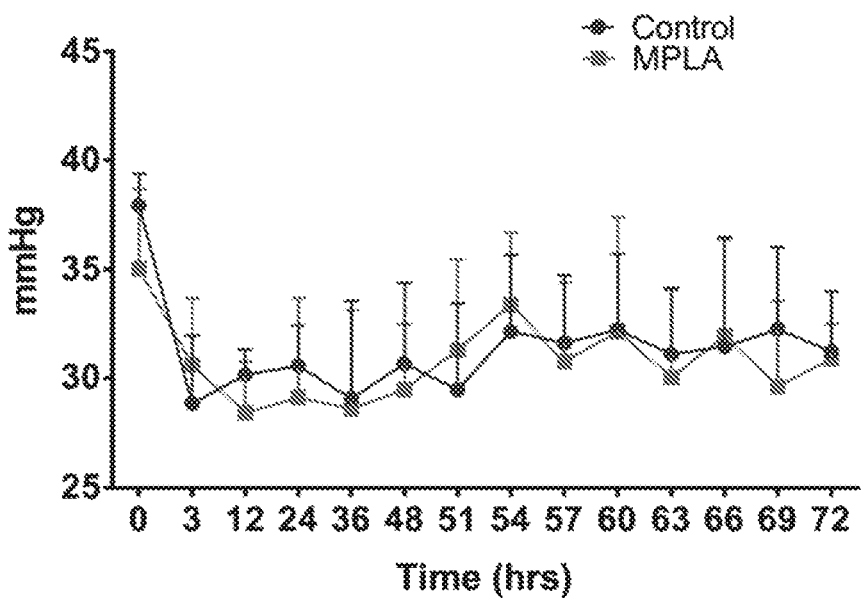
Figure 14:
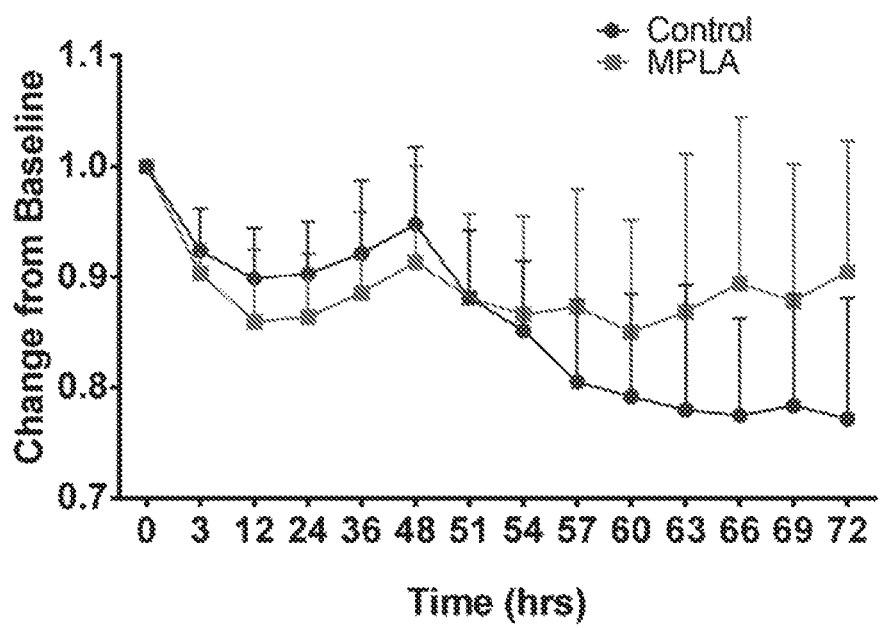
Figure 14:
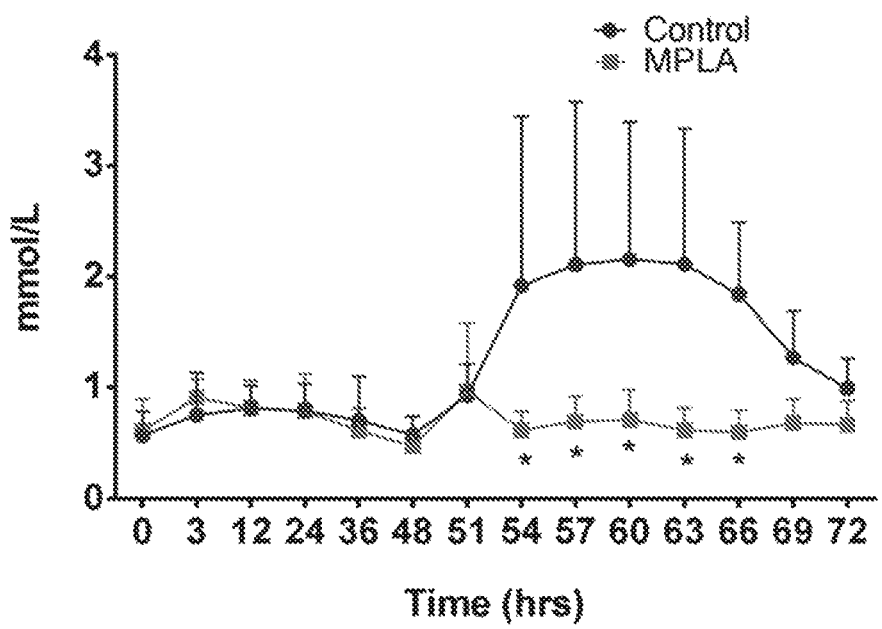

Given these results in non-burned sheep, a rigorous assessment of the response of burned sheep to MPLA infusion was performed (FIG. 7). Sheep were instrumented and received a 20% cutaneous burn. At 24 hours after the burn procedure, MPLA (5 ug/kg) was infused in 10 ml of endotoxin-free lactated Ringer's solution over 10 minutes. The sheep developed a transient 1° C. increase in core temperature at 1 hour after the start of infusion (FIG. 7). Heart rate and pulmonary artery pressure were not significantly altered. Cardiac index, mean arterial pressure, central venous pressure, stroke volume, systemic vascular resistance, peak and pause airway pressures and $PaO_2/FiO_2$ ratio were not significantly changed by MPLA infusion (FIG. 14). These data confirm that sheep respond to MPLA similarly to humans and that 5 ug/kg is a safe dose.

Physiological Impact of Intravenous and Intramuscular PHAD Administration and Dosing in Sheep.

Adult female sheep (30-40 kg) are surgically prepared for chronic study under isoflurane anesthesia as previously described (38, 39). Briefly, catheters are placed into the right femoral artery and the left atrium for continuous measurement of heart rate, blood pressure and left atrial pressure, respectively. A Swan-Ganz thermal dilution catheter is introduced through the right external jugular vein and advanced into the pulmonary artery for measurement of pulmonary arterial, central venous and pulmonary capillary wedge pressures, cardiac output and core body temperature The thoracic lymph duct draining the lung is cannulated via thoracotomy at the $5^{th}$ intercostal space. The cannula is exteriorized and secured for intermittent collection of lung lymph samples. Following the operative procedures, the sheep are awakened and given five to seven days to recover from the operative procedures. All vascular catheters are connected to physiological recorders via pressure transducers and accurate hemodynamic monitoring is initiated. For admission into the protocol, the animals must have a $PaO_2$>90 mmHg, a $PaCO_2$<36 mmHg, a body temperature greater than 38° C. and less than 40° C., a heart rate <100/min, a hematocrit >22 and a white count between 5,000 and 10,000 leukocytes/µl.

Sheep (n=6/group) undergo instrumentation as described above receive an intravenous infusion or intramuscular injection of PHADs at 3 different doses (2.5, 5 and 10 µg/kg) or vehicle. PHADs are infused in a volume of 10 mL over 10 minutes. For intramuscular administration, PHADs are administered at the doses described above (2.5, 5 or 10 µg/kg) in 1 ml of vehicle. During the ensuing 2 hours (for each dose and route), hemodynamic endpoints such as heart rate, mean arterial pressures, pulmonary arterial pressures, left atrial pressure, pulmonary capillary wedge pressures, central venous pressures, and cardiac output are measured at 0, 5, 10, 15, 30, 60, 90 and 120 minutes. Core body temperature is measured at the same time points. Blood is harvested at each time point for measurement of plasma IL-6 and IL-8 concentrations as well as determination of complete blood count and differential. Arterial blood gases are analyzed at 30-minute intervals with emphasis on evaluation of $pO_2$, pH, glucose and lactate concentrations. Hemodynamics are monitored hourly out to 24 hours after PHAD administration. Each sheep initially receives the 2.5 µg/kg dose. At 24 hours later, blood is obtained for measurement of plasma IL-6 and IL-8, arterial blood gases, CBC with differential and assessment of immunomodulation. For assessment of immunomodulation, the blood is mixed 50:50 with RPMI-1640 media containing LPS (100 ng/ml) or vehicle and incubated (37° C., 5% $CO_2$) for 24 hours. IL-6 and IL-8 concentrations in the liquid phase are measured by ELISA. An attenuation of LPS-induced IL-6 and IL-8 production, compared to control sheep, signifies induction of an immunomodulated phenotype.

After harvesting of 24 hour blood samples, the same sheep receive a PHAD at the 5 µg/kg dose via the same route of administration. Finally, the same sheep receive PHAD at the g/kg dose after harvesting the 24 hour samples from the 5 µg/kg dosing. This allows for testing of all 3 doses of each agent via either the intravenous or intramuscular route in the same sheep.

Pharmacokinetics Study.

Before and after the dosing of PHADs, arterial and mixed venous blood plasma, urine and pulmonary lymph are collected and stored at −80° C. for the pharmacokinetics analytical assays. The time points of sample collections are 0, 5, 10, 15, 30, 60, 90, and 120 minutes. A final sample is obtained at the 24-hour blood draw. PHAD concentrations in samples are determined using liquid chromatography and mass spectroscopy.

Evaluation of the Efficacy of PHADs Against *Pseudomonas aeruginosa*—and *Staphylococcus aureus*—Induced Pneumonia in Sheep.

The ability of PHADs to augment host resistance against *P. aeruginosa* and *S. aureus* infection is tested in sheep. These experiments allow establishment of the efficacy of PHADs in clinically relevant models of infection in an animal model that closely mimics the human condition.

Sheep are surgically prepared as described as above. After the 5-7 day surgical recovery period, sheep are intubated under intravenous ketamine anesthesia (5 mg/kg) and anesthesia is maintained using isoflurane. When corneal reflexes are inhibited, 0.01 mg/kg of intramuscular buprenorphine is administered and 40% total body surface area third-degree flame burn is made on both flanks by Bunsen burner as previously described (38, 39). After the injury, sheep are awakened, connected to the physiologic monitor and fluid resuscitated with lactated Ringer's solution is initiated. All sheep are monitored for 48 hours after the burn injury.

At 2 days after burn injury, PHADs are administered by the intravenous or intramuscular route. The physiological response to PHADs during the treatment period is determined as described above. Pharmacokinetics are measured during the treatment period as defined above.

At 48 hours after PHAD or vehicle treatment, *Pseudomonas aeruginosa* (~5×10$^6$ colony-forming units in 30-mL solution) or *Staphylococcus aureus* (~5×10$^8$ colony-forming units in 30-mL solution) are instilled into the airways through a bronchoscope as previously described (35, 36, 40, 41). Ten milliliters is placed in the right middle and lower and left lower lobes of the lung. After inoculation, sheep are maintained on mechanical ventilation (ARDSnet guidelines) and monitored in an awake condition throughout the 48 hour experimental period. All animals receive maintenance fluid resuscitation during the study period.

Physiologic monitoring is initiated according the guidelines above and values are recorded. Blood is harvested for bacterial culture, arterial blood gas analysis and cytokine (IL-6/IL-8) measurements at 3 hour intervals over a 48 hour period. Blood gas analyses focuses on $PaO_2/FiO_2$ ratio, pH, base deficit and lactate concentrations. At 48 hours after infection, sheep are euthanized. The lungs and other organs (liver, kidney, heart, and spleen) are harvested for measurement of *Pseudomonas* CFU, myeloperoxidase, wet to dry weight ratio and histological analysis to assess neutrophil infiltration. The plasma and urines samples are collected every 3 hours post injury.

REFERENCES CITED

1. Cen, H., Z. Wu, F. Wang, and C. Han. 2015. Pathogen distribution and drug resistance in a burn ward: a three-year retrospective analysis of a single center in China. Int J Clin Exp Med 8: 19188-19199.
2. Gladki, A., S. Kaczanowski, P. Szczesny, and P. Zielenkiewicz. 2013. The evolutionary rate of antibacterial drug targets. BMC Bioinformatics 14: 36.
3. Sun, H. Y., S. Fujitani, R. Quintiliani, and V. L. Yu. 2011. Pneumonia due to *Pseudomonas aeruginosa*: part II: antimicrobial resistance, pharmacodynamic concepts, and antibiotic therapy. Chest 139: 1172-1185.
4. Williams, F. N., D. N. Herndon, H. K. Hawkins, J. O. Lee, R. A. Cox, G. A. Kulp, C. C. Finnerty, D. L. Chinkes, and M. G. Jeschke. 2009. The leading causes of death after burn injury in a single pediatric burn center. Crit Care 13: R183.
5. George, A. J., A. K. Boehme, J. E. Siegler, D. Monlezun, B. D. Fowler, A. Shaban, K. C. Albright, T. M. Beasley, and S. Martin-Schild. 2013. Hospital-Acquired Infection Underlies Poor Functional Outcome in Patients with Prolonged Length of Stay. ISRN Stroke 2013.
6. Wenzel, R. P., and M. B. Edmond. 2001. The impact of hospital-acquired bloodstream infections. Emerg Infect Dis 7: 174-177.
7. Klevens, R. M., J. R. Edwards, and R. P. Gaynes. 2008. The impact of antimicrobial-resistant, health care-associated infections on mortality in the United States. Clin Infect Dis 47: 927-930.
8. Shlaes, D. M., D. Sahm, C. Opiela, and B. Spellberg. 2013. The FDA reboot of antibiotic development. Antimicrob Agents Chemother 57: 4605-4607.
9. Geyik, M. F., M. Aldemir, S. Hosoglu, and H. I. Tacyildiz. 2003. Epidemiology of burn unit infections in children. Am J Infect Control 31: 342-346.
10. Gang, R. K., R. L. Bang, S. C. Sanyal, E. Mokaddas, and A. R. Lari. 1999. *Pseudomonas aeruginosa* septicaemia in burns. Burns 25: 611-616.
11. Bang, R. L., P. N. Sharma, S. C. Sanyal, S. Bang, and M. K. Ebrahim. 2004. Burn septicaemia in Kuwait: associated demographic and clinical factors. Med Princ Pract 13: 136-141.
12. Laird, M. H., S. H. Rhee, D. J. Perkins, A. E. Medvedev, W. Piao, M. J. Fenton, and S. N. Vogel. 2009. TLR4/MyD88/PI3K interactions regulate TLR4 signaling. J Leukoc Biol 85: 966-977.
13. Bohannon, J. K., A. Hernandez, P. Enkhbaatar, W. L. Adams, and E. R. Sherwood. 2013. The immunobiology of toll-like receptor 4 agonists: from endotoxin tolerance to immunoadjuvants. Shock 40: 451-462.

14. Murphey, E. D., G. Fang, T. K. Varma, and E. R. Sherwood. 2007. Improved bacterial clearance and decreased mortality can be induced by LPS tolerance and is not dependent upon IFN-gamma. Shock 27: 289-295.
15. Murphey, E. D., G. Fang, and E. R. Sherwood. 2008. Endotoxin pretreatment improves bacterial clearance and decreases mortality in mice challenged with *Staphylococcus aureus*. Shock 29: 512-518.
16. Varma, T. K., M. Durham, E. D. Murphey, W. Cui, Z. Huang, C. Y. Lin, T. Toliver-Kinsky, and E. R. Sherwood. 2005. Endotoxin priming improves clearance of *Pseudomonas aeruginosa* in wild-type and interleukin-10 knockout mice. Infect Immun 73:7340-7347.
17. Lembo, A., M. Pelletier, R. Iyer, M. Timko, J. C. Dudda, T. E. West, C. B. Wilson, A. M. Hajjar, and S. J. Skerrett. 2008. Administration of a synthetic TLR4 agonist protects mice from pneumonic tularemia. J Immunol 180: 7574-7581.
18. Romero, C. D., T. K. Varma, J. B. Hobbs, A. Reyes, B. Driver, and E. R. Sherwood. 2011. The Toll-like receptor 4 agonist monophosphoryl lipid a augments innate host resistance to systemic bacterial infection. Infect Immun 79: 3576-3587.
19. Metkar, S., K. S. Kim, J. Silver, and S. M. Goyert. 2012. Differential expression of CD14-dependent and independent pathways for chemokine induction regulates neutrophil trafficking in infection. J Leukoc Biol 92: 389-396.
20. Hernandez, A., J. K. Bohannon, L. Luan, B. A. Fensterheim, Y. Guo, N. K. Patil, C. McAdams, J. Wang, and E. R. Sherwood. 2016. The role of MyD88- and TRIF-dependent signaling in monophosphoryl lipid A-induced expansion and recruitment of innate immunocytes. J Leukoc Biol.
21. Bohannon, J. K., L. Luan, A. Hernandez, A. Afzal, Y. Guo, N. K. Patil, B. Fensterheim, and E. R. Sherwood. 2015. Role of G-CSF in monophosphoryl lipid A-mediated augmentation of neutrophil functions after burn injury. J Leukoc Biol.
22. Krakauer, T., M. J. Buckley, and D. Fisher. 2010. Proinflammatory mediators of toxic shock and their correlation to lethality. Mediators Inflamm 2010: 517594.
23. Kiener, P. A., F. Marek, G. Rodgers, P. F. Lin, G. Warr, and J. Desiderio. 1988. Induction of tumor necrosis factor, IFN-gamma, and acute lethality in mice by toxic and non-toxic forms of lipid A. J Immunol 141: 870-874.
24. Astiz, M. E., E. C. Rackow, J. G. Still, S. T. Howell, A. Cato, K. B. Von Eschen, J. T. Ulrich, J. A. Rudbach, G. McMahon, R. Vargas, and et al. 1995. Pretreatment of normal humans with monophosphoryl lipid A induces tolerance to endotoxin: a prospective, double-blind, randomized, controlled trial. Crit Care Med 23: 9-17.
25. Bentala, H., W. R. Verweij, A. Huizinga-Van der Vlag, A. M. van Loenen-Weemaes, D. K. Meijer, and K. Poelstra. 2002. Removal of phosphate from lipid A as a strategy to detoxify lipopolysaccharide. Shock 18: 561-566.
26. Henricson, B. E., W. R. Benjamin, and S. N. Vogel. 1990. Differential cytokine induction by doses of lipopolysaccharide and monophosphoryl lipid A that result in equivalent early endotoxin tolerance. Infect Immun 58: 2429-2437.
27. Monie, A., C. F. Hung, R. Roden, and T. C. Wu. 2008. Cervarix: a vaccine for the prevention of HPV 16, 18-associated cervical cancer. Biologics 2: 97-105.
28. Bosch, F. X., S. de Sanjose, and X. Castellsague. 2011. The prospects of HPV vaccination in cervical cancer prevention: results of a new independent trial. Cancer Discov 1: 377-380.
29. Bohannon, J. K., L. Luan, A. Hernandez, A. Afzal, Y. Guo, N. K. Patil, B. Fensterheim, and E. R. Sherwood. 2015. Role of G-CSF in monophosphoryl lipid A-mediated augmentation of neutrophil functions after burn injury. J Leukoc Biol.
30. Bohannon, J., W. Cui, R. Cox, R. Przkora, E. Sherwood, and T. Toliver-Kinsky. 2008. Prophylactic treatment with fms-like tyrosine kinase-3 ligand after burn injury enhances global immune responses to infection. Journal of immunology 180: 3038-3048.
31. Bohannon, J., W. Cui, E. Sherwood, and T. Toliver-Kinsky. 2010. Dendritic cell modification of neutrophil responses to infection after burn injury. Journal of immunology 185: 2847-2853.
32. Redl, H., S. Bahrami, G. Schlag, and D. L. Traber. 1993. Clinical detection of LPS and animal models of endotoxemia. Immunobiology 187: 330-345.
33. Nakazawa, H., H. Noda, S. Noshima, J. T. Flynn, L. D. Traber, D. N. Herndon, and D. L. Traber. 1993. Pulmonary transvascular fluid flux and cardiovascular function in sheep with chronic sepsis. J Appl Physiol 75: 2521-2528.
34. Enkhbaatar, P., K. Murakami, L. D. Traber, R. Cox, J. F. Parkinson, M. Westphal, A. Esechie, N. Morita, M. O. Maybauer, D. M. Maybauer, A. S. Burke, F. C. Schmalstieg, H. K. Hawkins, D. N. Herndon, and D. L. Traber. 2006. The inhibition of inducible nitric oxide synthase in ovine sepsis model. Shock 25: 522-527.
35. Enkhbaatar, P., C. Joncam, L. Traber, Y. Nakano, J. Wang, M. Lange, R. Connelly, G. Kulp, F. Saunders, R. Huda, R. Cox, F. Schmalstieg, D. Herndon, and D. Traber. 2008. Novel ovine model of methicillin-resistant *Staphylococcus aureus*-induced pneumonia and sepsis. Shock 29: 642-649.
36. Sousse, L. E., C. C. Jonkam, D. L. Traber, H. K. Hawkins, S. W. Rehberg, L. D. Traber, D. N. Herndon, and P. Enkhbaatar. 2011. *Pseudomonas aeruginosa* is associated with increased lung cytokines and asymmetric dimethylarginine compared with methicillin-resistant *Staphylococcus aureus*. Shock 36: 466-470.
37. Enkhbaatar, P., C. Nelson, J. R. Salsbury, J. R. Carmical, K. E. Torres, D. Herndon, D. S. Prough, L. Luan, and E. R. Sherwood. 2015. Comparison of Gene Expression by Sheep and Human Blood Stimulated with the TLR4 Agonists Lipopolysaccharide and Monophosphoryl Lipid A. PLoS One 10: e0144345.
38. Enkhbaatar, P., A. Esechie, J. Wang, R. A. Cox, Y. Nakano, A. Hamahata, M. Lange, L. D. Traber, D. S. Prough, D. N. Herndon, and D. L. Traber. 2008. Combined anticoagulants ameliorate acute lung injury in sheep after burn and smoke inhalation. Clin Sci (Lond) 114: 321-329.
39. Cox, R. A., S. Jacob, G. Oliveras, K. Murakami, P. Enkhbaatar, L. Traber, F. C. Schmalstieg, D. N. Herndon, D. L. Traber, and H. K. Hawkins. 2009. Pulmonary expression of nitric oxide synthase isoforms in sheep with smoke inhalation and burn injury. Exp Lung Res 35: 104-118.
40. Lange, M., A. Hamahata, D. L. Traber, A. Esechie, C. Jonkam, K. Bansal, Y. Nakano, L. D. Traber, and P. Enkhbaatar. 2010. A murine model of sepsis following smoke inhalation injury. Biochem Biophys Res Commun 391: 1555-1560.

41. Jonkam, C. C., K. Bansal, D. L. Traber, A. Hamahata, M. O. Maybauer, D. M. Maybauer, R. A. Cox, M. Lange, R. L., Connelly, L. D. Traber, C. D. Djukom, J. R. Salsbury, D. N. Herndon, and P. Enkhbaatar. 2009. Pulmonary vascular permeability changes in an ovine model of methicillin-resistant *Staphylococcus aureus* sepsis. Crit Care 13: R19.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method for treating or preventing a bacterial infection or a fungal infection, comprising administering to a subject in need thereof a therapeutically effective amount of an active agent, wherein the active agent consists essentially of phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof, wherein the subject is recovering from surgery or the subject is recovering from trauma.

2. The method of claim 1, wherein the active agent is phosphorylated hexaacyl disaccharide (PHAD).

3. The method of claim 1, wherein the active agent is 3-deacyl phosphorylated hexaacyl disaccharide (3D-PHAD).

4. The method of claim 1, wherein the active agent is 3-D (6-acyl) phosphorylated hexaacyl disaccharide (3D(6-acyl) PHAD).

5. The method of claim 1, wherein the bacterial infection is a multi-drug resistant strain.

6. The method of claim 1, wherein the bacterial infection is selected from *Pseudomonas aeruginosa* or *Staphylococcus aureus*.

7. The method of claim 1, wherein the bacterial infection is a gram-negative bacteria.

8. The method of claim 1, wherein the trauma is a burn.

9. The method of claim 1, wherein the fungal infection is *Candida albicans*.

10. A method for treating or preventing a bacterial infection or a fungal infection, comprising administering to a subject in need thereof a therapeutically effective amount of a pharmaceutical composition comprising an active agent, wherein the active agent consists essentially of phosphorylated hexaacyl disaccharide (PHAD), 3-deacyl phosphorylated hexaacyl disaccharide (3D-PHAD), 3-D (6-acyl) phosphorylated hexaacyl disaccharide (3D(6-acyl) PHAD), or a pharmaceutically acceptable salt thereof, and a pharmaceutically acceptable carrier, wherein the subject is recovering from surgery or the subject is recovering from trauma.

11. The method of claim 10, wherein the active agent is phosphorylated hexaacyl disaccharide (PHAD).

12. The method of claim 10, wherein the active agent is 3-deacyl phosphorylated hexaacyl disaccharide (3D-PHAD).

13. The method of claim 10, wherein the active agent is 3-D (6-acyl) phosphorylated hexaacyl disaccharide (3D(6-acyl) PHAD).

14. The method of claim 10, wherein the bacterial infection is a multi-drug resistant strain.

15. The method of claim 10, wherein the bacterial infection is selected from *Pseudomonas aeruginosa* or *Staphylococcus aureus*.

16. The method of claim 10, wherein the bacterial infection is a gram-negative bacteria.

\* \* \* \* \*